US008470334B2

(12) United States Patent
Barnett et al.

(10) Patent No.: US 8,470,334 B2
(45) Date of Patent: Jun. 25, 2013

(54) METHOD OF INDUCING AN ANTIVIRAL IMMUNE RESPONSE AGAINST HIV-1 UTILIZING CHIMERIC HIV ENV PROTEINS COMPRISING CD4 MINI-PROTEINS OR CD4 MIMETICS

(75) Inventors: Susan W. Barnett, San Francisco, CA (US); Indresh K. Srivastava, Benicia, CA (US)

(73) Assignee: Novartis Vaccines & Diagnostics, Inc, Emeryville, CA (US)

( * ) Notice: Subject to any disclaimer, the term of this patent is extended or adjusted under 35 U.S.C. 154(b) by 0 days.

(21) Appl. No.: 13/544,063

(22) Filed: Jul. 9, 2012

(65) Prior Publication Data

US 2012/0276128 A1 Nov. 1, 2012

Related U.S. Application Data

(66) Division of application No. 12/859,356, filed on Aug. 19, 2010, now Pat. No. 8,226,955, which is a division of application No. 10/514,055, filed as application No. PCT/US03/14575 on May 7, 2003, now Pat. No. 7,811,580, Substitute for application No. 60/378,543, filed on May 7, 2002.

(60) Provisional application No. 60/459,314, filed on Mar. 31, 2003.

(51) Int. Cl.

*A61K 39/00* (2006.01)
*A61K 39/21* (2006.01)
*A61K 38/00* (2006.01)

(52) U.S. Cl.

USPC .................... 424/192.1; 424/208.1; 530/324; 536/23.72

(58) Field of Classification Search

None

See application file for complete search history.

(56) References Cited

U.S. PATENT DOCUMENTS

| | | | |
|---|---|---|---|
| 4,708,871 | A | 11/1987 | Geysen |
| 5,518,723 | A | 5/1996 | DeVico et al. |
| 5,714,316 | A | 2/1998 | Weiner et al. |
| 5,843,454 | A | 12/1998 | DeVico et al. |
| 6,030,772 | A | 2/2000 | DeVico et al. |

FOREIGN PATENT DOCUMENTS

| | | | |
|---|---|---|---|
| WO | 9419017 | A1 | 9/1994 |
| WO | 9604301 | A2 | 2/1996 |
| WO | 0039302 | A2 | 7/2000 |
| WO | 0039303 | A2 | 7/2000 |
| WO | 0127294 | A1 | 4/2001 |
| WO | 0130814 | A1 | 5/2001 |
| WO | 03020876 | A2 | 3/2003 |
| WO | 2004014420 | | 2/2004 |

OTHER PUBLICATIONS

Vita et al., 1999, Rational engineering of a miniprotein that reproduces the core of teh CD4 site interacting with HIV-1 envelope glycoprotein, Proc. Natl. Acad. Sci. USA 96:13091-13096.*

Martin et al., 2003, Rational design of a CD4 mimetic that inhibits HIV-1 entry and exposes cryptic neutralization epitopes, Nat. Biotech. 21:71-76.*

Barre-Sinoussi et al., "Isolation of a T-Lymphotropic Retrovirus from a Patient at Risk for Acquired Immune Deficiency Syndrome (AIDS)," Science 220, 868-71, 1983.

Arthos et al., "Identification of the Residues in Human CD4 Critical for the Binding of HIV," Cell 57, 469-81, 1989.

Binley et al., "An Investigation of the High-Avidity Antibody Response to Glycoprotein 120 of Human Immunodeficiency Virus Type 1," AIDS Res. Hum. Retroviruses 13, 1007-15, 1997.

Bolognesi et al., "HIV Vaccine Development: A Progress Report," Ann. Int. Med. 8, 603-11, 1994.

Burton & Montefiore, "The antibody response in HIV-1 infection," AIDS 11 (Suppl. A), 587-98, 1997.

Clackson & Wells, "A Hot Spot of Binding Energy in a Hormone-Receptor Interface," Science 267, 383-86, 1995.

DeVico et al., "Monoclonal Antibodies Raised Against Covalently Crosslinked of Human Immunodeficiency Type 1 gp120 and CD4 Receptor Identify a Novel Complex-Dependent Epitope on gp120," Virol. 211, 583-88, 1995.

DeVico et al., "Covalently Crosslinked Complexes of Human Immunodeficiency Virus Type 1 (HIV-1) gp120 and CD4 Receptor Elicit a Neutralizing Immune Response That Includes Antibodies Selective for Primary Virus Isolates," Virology 218, 258-63, 1996.

D'Sousa et al., "Evaluation of Monoclonal Antibodies to Human Immunodeficiency Virus Type 1 Primary Isolates by Neutralization Assays: Performance Criteria for Selecting Candidate Antibodies for Clinical Trials," J. Infect. Dis. 75, 1062-75, 1997.

Fiore et al., "The Biological Phenotype of HIV-1 is Usually Retained During and After Sexual Transmission," Virol. 204, 297-303, 1994.

Gallo et al., "Frequent Detection and Isolation of Cytopathic Retroviruses (HTLV-III) from Patients with AIDS and at Risk for AIDS," "Serological Analysis of a Subgroup of Human T-Lymphotropic Retroviruses (HTLV-III) Associated with AIDS," Science 224, 500-03, 1984.

Database PIR Entry A03976 (Entry VCLJA2), May 17, 1985.

Gershoni et al., "HIV Binding to Its Receptor Creates Specific Epitopes for the CD4/gp120 Complex," FASEB J. 7, 1185-87, 1993.

Geysen et al., "A Priori Delineation of a Peptide Which Mimics a Discontinuous Antigenic Determinant," Mol. Immunol. 23, 709-15, 1986.

Geysen et al., "Use of peptide synthesis to probe viral antigens for epitopes to a resolution of a single amino acid," Proc. Natl. Acad. Sci. USA 81, 3998-4002, 1984.

Guyader et al., "Genome Organization and Transactivation of the Human Immunodeficiency Virus Type 2," Nature 326, 662-69, 1987.

Haynes et al., "Toward an Understanding of the Correlates of Protective Immunity to HIV Infection," Science 271, 324-28, 1996.

Hu et al., "Protection of Macaques Against SIV Infection by Subunit Vaccines of SIV Envelope Glycoprotein gpl60," Science 255, 456-59, 1992.

(Continued)

*Primary Examiner* — Jeffrey S. Parkin

(74) *Attorney, Agent, or Firm* — Helen Lee; Regina Bautista

(57) ABSTRACT

Env-CD4 polypeptide complexes and hybrids that expose cryptic epitopes important in virus neutralization are disclosed. Methods of diagnosis, treatment and prevention using the polypeptides are also provided.

28 Claims, 7 Drawing Sheets

OTHER PUBLICATIONS

Javaherian et al., "Principal neutralizing domain of the human immunodeficiency virus type 1 envelope protein," Proc. Natl. Acad. Sci. USA 86, 6786-72, 1989.
Kwong et al., "Structure of an HIVgp120 envelope glycoprotein in complex with the CD4 receptor and a neutralizing human antibody," Nature 393, 648-59, 1998.
Lacasset et al., "Fusion-Competent Vaccines: Broad Neutralizations of Primary Isolates of HIV," Science 283, 357-62, 1999.
Leu et al., "Immunogenicity of DNA Vaccines Expressing Human Immunodeficiency Virus Type 1 Envelope Glycoprotein with and without Deletions in the V1/V2 and V3 Regions," AIDS Res. and Human Retroviruses 14, 151-55, 1998.
Levy et al., "Isolation of Lymphocytopathic Retroviruses from San Francisco Patients with AIDS," Science 225, 840-42, 1984.
Martin et al., "Rational Design of a CD4 Mimic that Inhibits HIV-1 Entry and Exposes Cryptic Neutralization Epitopes," Nat. Biotech. 21, 71-76, 2003.
Mascola et al., "Immunization with Envelope Subunit Vaccine Products Elicits Neutralizing Antibodies against Laboratory-Adapted but not Primary Isolates of Human Immunodeficiency Virus Type 1," J. Infect. Dis. 173, 340-48, 1996.
Matsushita et al., "Characterization of a Human Immunodeficiency Virus Neutralizing Monoclonal Antibody and Mapping of the Neutralizing Epitope," J. Virol. 62, 2107-44, 1988.
Matthews, "Restricted neutralization of divergent human T-lymphotropic virus type III isolates by antibodies to the major envelope glycoprotein," Proc. Natl. Acad. Sci. USA 83, 9709-13, 1986.
Montefiori & Evans, "Toward an HIV Type 1 Vaccine that Generates Potent, Broadly Cross-Reactive Neutralizing Antibodies," AIDS Res. Hum. Retroviruses 15, 689-98, 1999.
Nara et al., "Purified Envelope Glycoproteins from Human Immunodeficiency Virus Type 1 Variants Induce Individual, Type-Specific Neutralizing Antibodies," J. Virol. 62, 2622-28, 1988.
Palker et al., "Type-specific neutralization of the human immunodeficiency virus with antibodies to env-encoded synthetic peptides," Proc. Natl. Acad. Sci. USA 85, 1932-36, 1988.
Putney et al., "HTLV-III/LAV-Neutralizing Antibodies to an *E. coli*-Produced Fragment of the Virus Envelope," Science 234, 1392-95, 1986.
Ratner et al., "Complete Nucleotide of the AIDS Virus, HTLV-III," Nature 313, 277-84, 1985.
Rizzuto et al., "A Conserved HIV gp120 Glycoprotein Structure Involved in Chemokine Receptor Binding," Science 280, 1949-53, 1998.
Robert-Guroff et al., "HTLV-III-Neutralizing Antibodies in Patients with AIDS and AIDS-Related Complex," nature 316, 72-73, 1985.
Rushe et al., "Antibodies that inhibit fusion of human immunodeficiency virus-infected cells bind a 24-amino acid sequence of the viral envelope, gp120," Proc. Natl. Acad. Sci. USA 85, 3198-202, 1988.
Ryu et al., "Structures of an HIV and MHC binding fragment from human CD4 as refined in two crystal lattices," Structure 2, 59-74, 1994.
Sanchez-Pescador et al., "Nucleotide Sequence and Expression of an AIDS-Associated Retrovirus (ARV-2)," Science 227, 484-92, 1985.
Siegal et al., "Severe Acquired Immunodificiency in Male Homosexuals, Manifested by Chronic Perianal Ulcerative Herpes Simplex Lesions," N. Engl. J. Med. 305, 1439-44, 1981.
Stamatatos et al., "An Envelope Modification That Renders a Primary, Neutralization-Resistant Clade B Human Immunodeficiency Virus Type 1 Isolate Highly Susceptible to Neutralization by Sera from Other Clades," J. Virol. 72, 7840-45, 1998.
Stamatotos et al., "Effect of Major Deletions in the V1 and V2 Loops of a Macrophage-Tropic HIV Type 1 Isolate on Viral Envelope Structure, Cell Entry and Replication," AIDS Res. Hum. Retroviruses 14, 1129-39, 1998.
Sullivan et al., "Determinants of Human Immunodeficiency Virus Type 1 Envelope Glycoprotein Activation by Soluble CD4 and Monoclonal Antibodies," J. Virol. 72, 6332-38, 1998.
Thali et al., "Characterization of Conserved Human Immunodeficiency Virus Type 1 gpl20 Neutralization Epitopes Exposed upon gpl20-CD4 Binding," J. Virol. 67, 3978-88, 1993.
Trkola et al., "Cross-Clade Neutralization of Primary Isolates of Human Immunodeficiency Virus Type 1 by Human Monoclonal Antibodies and Tetrameric CD4-IgG," J. Viol. 69, 6609-17, 1995.
Truneh et al., "A Region in Domain 1 of CD4 Distinct from the Primary gp120 Binding Site Is Involved in HIV Infection and Virus-mediated Fusion," J. Biol. Chem. 266, 5942-48, 1991.
Vita et al., "Novel Miniproteins Engineered by the Transfer of Active Sites to Small Natural Scaffolds," Biopolymers 47, 93-100, 1998.
Vita et al., "Rational engineering of a miniprotein that reproduces the core of the CD4 site interacting with HIV-1 envelope glycoprotein," Proc. Natl. Acad. Sci. USA 96, 13091-96, 1999.
Vu et al., "An Immunoglobulin Fusion Protein Based on the gp120-CD4 Receptor Complex Potently Inhibits Human Immunodeficiency Virus Type 1 in Vitro," AIDS Res. Human Retroviruses 22, 477-90, 2006.
Weis et al., "Neutralization of Human T-Lymphotropic Virus Type III by Sera of AIDS and AIDS-Risk Patients," Nature 316, 69-72, 1985.
Weis et al., "Variable and Conserved Neutralization Antigens of Human Immunodeficiency Virus," Nature 324, 572-75, 1986.
Wyatt et al., "Involvement of the V1/V2 Variable Loop Structure in the Exposure of Human Immunodeficiency Virus Type 1 gp120 Epitopes Induced by Receptor Binding," J. Virol. 69, 5723-33, 1995.
Kang et al., Immunization with a soluble CD4-gp120 complex preferentially induces neutralizing anti-human Immunodeficiency Virus Type 1 Antibodies Directed to Conformation-Dependent Epitopes of gp120, Journal of Virology, vol. 68, No. 9, Sep. 1994, pp. 5854-5862.
Fouts et al., "Expression and Characterization of a Single-Chain Polypeptide Analogue of the Human Immunodeficiency Virus Type 1 gp120-CD4 Receptor Complex," Journal of Virology, vol. 74, No. 24, Dec. 2000, pp. 11427-11436.
Celada et al., "Antibody Raised Against Soluble CD4-rgp120 Complex Recognizes the CD4 Moiety and Blocks Membrane Fusion without Inhibiting CD4-gp120 Binding," Journal of Experimental Medicine, vol. 172, Oct. 1990, pp. 1143-1150.
Devico et al., "Immunogenic properties of HIV gp120-CD4 Complexes," Journal of Human Virology, vol. 5, No. 1, Jan. 2002, pp. 71.
Wyatt et al., "The antigenic structure of the HIVgp120 envelope glycoprotein," Nature 393, 705-11, 1998.
Zagury et al., "Long-Term Cultures of HTLV-III-Infected T Cells: A Model of Cytopathology of T-Cell Depletion in AIDS," Science 231, 850-53, 1986.
Zhang et al., "Conformational Changes of gp120 in Epitopes near the CCR5 Binding Site Are Induced by CD4 and a CD4 Miniprotein Mimetic," Biochemistry 38, 9405-16, 1999.
Zhu et al., "Genotypic and Phenotypic Characterization of HIV-1 in Patients with Primary Infection," Science 261, 1179-81, 1993.
Dash, B., et al., 1994, Deletion of a sing N-linked glycosylation site from the transmembrane envelope protein of human immunodeficiency virus type 1 stops cleavage and transport of gp160 preventing env-mediated fusion, J. Gen. Virol. 75(6): 1389-1397.
Lu, S., et al., 1998, Immunogenicity of DNA vaccines expressing human immunodeficiency virus type 1 envelope glycoprotein with and without deletions in the V1/2 and V3 regions, AIDS Res. Human Retrovir. 14(2): 151-5.
Gallo, R.C., 2005, The end of the beginning of the drive to an HIV-preventive vaccine: a view from over 20 years, the Lancet 366: 1894-1898.
Burton, D.R., et al., 2004, HIV vaccine design and the neutralizing antibody problem, Nat. Immunol. 5(3): 233-236.

* cited by examiner

```
  1 MKVKGTRRNY QHLWRWGTLL LGMLMICSAT EKLWVTVYYG VPVWKEATTT LFCASDARAY
 61 DTEVHNVWAT HACVPTDPNP QEVVLGNVTE NFNMWKNNMV EQMQEDIISL WDQSLKPCVK
121 LTPLCVTLNC TDLGKATNTN SSNWKEEIKG EIKNCSFNIT TSIRDKIQKE NALFRNLDVV
181 PIDNASTTTN YTNYRLIHCN RSVITQACPK VSFEPIPIHY CTPAGFAILK CNNKTFNGKG
241 PCTNVSTVQC THGIRPIVST QLLLNGSLAE EEVVIRSDNF TNNAKTIIVQ LNESVAINCT
301 RPNNNTRKSI YIGPGRAFHT TGRIIGDIRK AHCNISRAQW NNTLEQIVKK LREQFGNNKT
361 IVFNQSSGGD PEIVMHSFNC RGEFFYCNTT QLFNNTWRLN HTEGTKGNDT IILPCRIKQI
421 INMWQEVGKA MYAPPIGGQI SCSSNITGLL LTRDGGTNVT NDTEVFRPGG GDMRDNWRSE
481 LYKYKVIKIE PLGIAPTKAK RRVVQREKRA VGIVGAMFLG FLGAAGSTMG AVSLTLTVQA
541 RQLLSGIVQQ QNNLLRAIEA QQHLLQLTVW GIKQLQARVL AVERYLRDQQ LLGIWGCSGK
601 LICTTAVPWN ASWSNKSLED IWDNMTWMQW EREIDNYTNT IYTLLEESQN QQEKNEQELL
661 ELDKWASLWN WFSITNWLWY IKIFIMIVGG LVGLRIVFAV LSIVNRVRQG YSPLSFQTRL
721 PVPRGPDRPD GIEEEGGERD RDRSVRLVDG FLALIWEDLR SLCLFSYRRL RDLLLIAART
781 VEILGHRGWE ALKYWWSLLQ YWIQELKNSA VSWLNATAIA VTEGTDRVIE VAQRAYRAIL
841 HIHRRIRQGL ERLLL
```

Figure 1 (SEQ ID NO:6)

```
                                      Q I K I L G N Q G S F L T K G P     h CD4
                                      33                           48     (CDR2)
A F C N L R M C Q L S C R S L G L L G K C I G D K C E C V K H             scyllatoxin
1                                                             31
- - C N L A R C Q L S C K S L G L K G G C Q G S F C T C G - -             CD4 M3
    1                                                   27
- - C N L A R C Q L S C K S L G L K G G C A G S F C A C G - -             CD4 M8

- - C N L A R C Q L R C K S L G L L G K C A G S F C A C G P -             CD4 M9
```

Figure 2 (SEQ ID NO:7)

gp120mod.SF162

AMINO ACID SEQUENCE:

ATMDAMKRGLCCVLLLCGAVFVSPSAVEKLWVTVYYGVPVWKEATTTLFCASDAKAYDTEVHNVWATHACVPTDPNPQEIVLENV
TENFNMWKNNMVEQMHEDIISLWDQSLKPCVKLTPLCVTLHCTNLKNATNTKSSNWKEMDRGEIKNCSFKVTTSIRNKMQKEYAL
FYKLDVVPIDNDNTSYKLINCNTSVITQACPKVSFEPIPIHYCAPAGFAILKCNDKKFNGSGPCTNVSTVQCTHGIRPVVSTQLLLNGSL
AEEGVVIRSENFTDNAKTIIVQLKESVEIN*CTRPNNNTRKSITIGPGRAFYATGDIIGDIRQAH*CNISGEKWNNTLKQIVTKLQAQFGNKTIV
FKQSSGGDPEIVMHSFNCGGEFFYCNSTQLFNSTWNNTIGPNNTNGTITLPCRIKQIINRWQEVGKAMYAPPIRGQIRCSSNITGLLLT
RDGGKEISNTTEIFRPGGGDMRDNWRSELYKYKVVKIEPLGVAPTKAKRRVVQREKR*

Figure 7 (SEQ ID NO:5)

SEQUENCE LISTING

```
<160> NUMBER OF SEQ ID NOS: 7

<210> SEQ ID NO 1
<211> LENGTH: 92
<212> TYPE: PRT
<213> ORGANISM: Artificial Sequence
<220> FEATURE:
<223> OTHER INFORMATION: CD4 miniprotein
<220> FEATURE:
<221> NAME/KEY: MISC_FEATURE
<222> LOCATION: (1)..(5)
<223> OTHER INFORMATION: Linker residues that provide flexibility to
      gp120-CD4 for making a complex
<220> FEATURE:
<221> NAME/KEY: MISC_FEATURE
<222> LOCATION: (15)..(15)
<223> OTHER INFORMATION: In contact with gp120
<220> FEATURE:
<221> NAME/KEY: MISC_FEATURE
<222> LOCATION: (17)..(17)
<223> OTHER INFORMATION: In contact with gp120
<220> FEATURE:
<221> NAME/KEY: MISC_FEATURE
<222> LOCATION: (19)..(19)
<223> OTHER INFORMATION: In contact with gp120
<220> FEATURE:
<221> NAME/KEY: MISC_FEATURE
<222> LOCATION: (19)..(19)
<223> OTHER INFORMATION: In contact with gp120
<220> FEATURE:
<221> NAME/KEY: MISC_FEATURE
<222> LOCATION: (21)..(21)
<223> OTHER INFORMATION: In contact with gp120
<220> FEATURE:
<221> NAME/KEY: MISC_FEATURE
<222> LOCATION: (24)..(27)
<223> OTHER INFORMATION: In contact with gp120
<220> FEATURE:
<221> NAME/KEY: MISC_FEATURE
<222> LOCATION: (32)..(40)
<223> OTHER INFORMATION: In contact with gp120
<220> FEATURE:
<221> NAME/KEY: MISC_FEATURE
<222> LOCATION: (44)..(45)
<223> OTHER INFORMATION: In contact with gp120
<220> FEATURE:
<221> NAME/KEY: MISC_FEATURE
<222> LOCATION: (51)..(56)
<223> OTHER INFORMATION: In contact with gp120
<220> FEATURE:
<221> NAME/KEY: MISC_FEATURE
<222> LOCATION: (88)..(92)
<223> OTHER INFORMATION: Linker residues that provide flexibility to
      gp120-CD4 for making a complex
```

<400> SEQUENCE: 1

Gly Gly Gly Gly Gly Thr Cys Thr Ala Ser Gln Gln Lys Lys Ser Ile
1               5                   10                  15

Gln Phe His Trp Lys Asn Ser Asn Gln Ile Lys Ile Leu Gly Asn Gln
            20                  25                  30

Gly Ser Phe Leu Thr Lys Gly Pro Ser Lys Leu Asn Ile Arg Ala Asp
        35                  40                  45

Ser Arg Arg Ser Leu Trp Asp Gln Gly Asn Phe Pro Leu Ile Ile Lys
    50                  55                  60

Asn Leu Lys Ile Glu Asp Ser Asp Thr Tyr Ile Cys Glu Val Glu Asp
65                  70                  75                  80

Gln Lys Glu Glu Val Gln Leu Gly Gly Gly Gly Gly
                85                  90

<210> SEQ ID NO 2
<211> LENGTH: 76
<212> TYPE: PRT
<213> ORGANISM: Artificial Sequence
<220> FEATURE:
<223> OTHER INFORMATION: CD4 mini-protein
<220> FEATURE:
<221> NAME/KEY: MISC_FEATURE
<222> LOCATION: (1)..(5)
<223> OTHER INFORMATION: Linker residues that provide flexibility to gp120-CD4 for making a complex
<220> FEATURE:
<221> NAME/KEY: MISC_FEATURE
<222> LOCATION: (9)..(9)
<223> OTHER INFORMATION: In contact with gp120
<220> FEATURE:
<221> NAME/KEY: MISC_FEATURE
<222> LOCATION: (11)..(11)
<223> OTHER INFORMATION: In contact with gp120
<220> FEATURE:
<221> NAME/KEY: MISC_FEATURE
<222> LOCATION: (13)..(13)
<223> OTHER INFORMATION: In contact with gp120
<220> FEATURE:
<221> NAME/KEY: MISC_FEATURE
<222> LOCATION: (15)..(15)
<223> OTHER INFORMATION: In contact with gp120
<220> FEATURE:
<221> NAME/KEY: MISC_FEATURE
<222> LOCATION: (18)..(21)
<223> OTHER INFORMATION: In contact with gp120
<220> FEATURE:
<221> NAME/KEY: MISC_FEATURE
<222> LOCATION: (26)..(34)
<223> OTHER INFORMATION: In contact with gp120
<220> FEATURE:
<221> NAME/KEY: MISC_FEATURE
<222> LOCATION: (38)..(39)
<223> OTHER INFORMATION: In contact with gp120
<220> FEATURE:
<221> NAME/KEY: MISC_FEATURE
<222> LOCATION: (45)..(50)
<223> OTHER INFORMATION: In contact with gp120
<220> FEATURE:
<221> NAME/KEY: MISC_FEATURE
<222> LOCATION: (72)..(76)
<223> OTHER INFORMATION: Linker residues that provide flexibility to gp120-CD4 for making a complex

<400> SEQUENCE: 2

Gly Gly Gly Gly Gly Gln Lys Lys Ser Ile Gln Phe His Trp Lys Asn
1               5                   10                  15

Ser Asn Gln Ile Lys Ile Leu Gly Asn Gln Gly Ser Phe Leu Thr Lys
            20                  25                  30

Gly Pro Ser Lys Leu Asn Ile Arg Ala Asp Ser Arg Arg Ser Leu Trp
        35                  40                  45

-continued

```
Asp Gln Gly Asn Phe Pro Leu Ile Ile Lys Asn Leu Lys Ile Glu Asp
    50                  55                  60

Ser Asp Thr Tyr Ile Cys Glu Gly Gly Gly Gly Gly
65                  70                  75
```

<210> SEQ ID NO 3
<211> LENGTH: 47
<212> TYPE: PRT
<213> ORGANISM: Artificial Sequence
<220> FEATURE:
<223> OTHER INFORMATION: CD4 miniprotein
<220> FEATURE:
<221> NAME/KEY: MISC_FEATURE
<222> LOCATION: (1)..(5)
<223> OTHER INFORMATION: Linker residues that provide flexibility to gp120-CD4 for making a complex
<220> FEATURE:
<221> NAME/KEY: MISC_FEATURE
<222> LOCATION: (8)..(11)
<223> OTHER INFORMATION: In contact with gp120
<220> FEATURE:
<221> NAME/KEY: MISC_FEATURE
<222> LOCATION: (16)..(24)
<223> OTHER INFORMATION: In contact with gp120
<220> FEATURE:
<221> NAME/KEY: MISC_FEATURE
<222> LOCATION: (28)..(29)
<223> OTHER INFORMATION: In contact with gp120
<220> FEATURE:
<221> NAME/KEY: MISC_FEATURE
<222> LOCATION: (35)..(40)
<223> OTHER INFORMATION: In contact with gp120
<220> FEATURE:
<221> NAME/KEY: MISC_FEATURE
<222> LOCATION: (43)..(47)
<223> OTHER INFORMATION: Linker residues that provide flexibility to gp120-CD4 for making a complex

<400> SEQUENCE: 3

```
Gly Gly Gly Gly Gly Asn Ser Asn Gln Ile Lys Ile Leu Gly Asn Gln
1               5                   10                  15

Gly Ser Phe Leu Thr Lys Gly Pro Ser Lys Leu Asn Ile Arg Ala Asp
            20                  25                  30

Ser Arg Arg Ser Leu Trp Asp Gln Gly Asn Gly Gly Gly Gly Gly
        35                  40                  45
```

<210> SEQ ID NO 4
<211> LENGTH: 39
<212> TYPE: PRT
<213> ORGANISM: Artificial Sequence
<220> FEATURE:
<223> OTHER INFORMATION: CD4 miniprotein
<220> FEATURE:
<221> NAME/KEY: MISC_FEATURE
<222> LOCATION: (1)..(5)
<223> OTHER INFORMATION: Linker residues that provide flexibility to gp120-CD4 for making a complex
<220> FEATURE:
<221> NAME/KEY: MISC_FEATURE
<222> LOCATION: (8)..(16)
<223> OTHER INFORMATION: In contact with gp120
<220> FEATURE:
<221> NAME/KEY: MISC_FEATURE
<222> LOCATION: (20)..(21)
<223> OTHER INFORMATION: In contact with gp120
<220> FEATURE:
<221> NAME/KEY: MISC_FEATURE
<222> LOCATION: (27)..(32)
<223> OTHER INFORMATION: In contact with gp120
<220> FEATURE:
<221> NAME/KEY: MISC_FEATURE
<222> LOCATION: (35)..(39)
<223> OTHER INFORMATION: Linker residues that provide flexibility to gp120-CD4 for making a complex

<400> SEQUENCE: 4

Gly Gly Gly Gly Gly Gly Asn Gln Gly Ser Phe Leu Thr Lys Gly Pro
1               5                   10                  15

Ser Lys Leu Asn Ile Arg Ala Asp Ser Arg Arg Ser Leu Trp Asp Gln
            20                  25                  30

Gly Asn Gly Gly Gly Gly Gly
        35

<210> SEQ ID NO 5
<211> LENGTH: 499
<212> TYPE: PRT
<213> ORGANISM: Artificial Sequence
<220> FEATURE:
<223> OTHER INFORMATION: gp120.modSF62
<220> FEATURE:
<221> NAME/KEY: MISC_FEATURE
<222> LOCATION: (127)..(151)
<223> OTHER INFORMATION: V1 loop
<220> FEATURE:
<221> NAME/KEY: MISC_FEATURE
<222> LOCATION: (152)..(191)
<223> OTHER INFORMATION: V2 loop
<220> FEATURE:
<221> NAME/KEY: MISC_FEATURE
<222> LOCATION: (291)..(324)
<223> OTHER INFORMATION: V3 loop
<220> FEATURE:
<221> NAME/KEY: MISC_FEATURE
<222> LOCATION: (378)..(405)
<223> OTHER INFORMATION: V4 loop
<220> FEATURE:
<221> NAME/KEY: MISC_FEATURE
<222> LOCATION: (447)..(459)
<223> OTHER INFORMATION: V5 loop

<400> SEQUENCE: 5

Ala Thr Met Asp Ala Met Lys Arg Gly Leu Cys Cys Val Leu Leu Leu
1               5                   10                  15

Cys Gly Ala Val Phe Val Ser Pro Ser Ala Val Glu Lys Leu Trp Val
            20                  25                  30

Thr Val Tyr Tyr Gly Val Pro Val Trp Lys Glu Ala Thr Thr Thr Leu
        35                  40                  45

Phe Cys Ala Ser Asp Ala Lys Ala Tyr Asp Thr Glu Val His Asn Val
    50                  55                  60

Trp Ala Thr His Ala Cys Val Pro Thr Asp Pro Asn Pro Gln Glu Ile
65                  70                  75                  80

Val Leu Glu Asn Val Thr Glu Asn Phe Asn Met Trp Lys Asn Asn Met
                85                  90                  95

Val Glu Gln Met His Glu Asp Ile Ile Ser Leu Trp Asp Gln Ser Leu
            100                 105                 110

Lys Pro Cys Val Lys Leu Thr Pro Leu Cys Val Thr Leu His Cys Thr
        115                 120                 125

Asn Leu Lys Asn Ala Thr Asn Thr Lys Ser Ser Asn Trp Lys Glu Met
    130                 135                 140

Asp Arg Gly Glu Ile Lys Asn Cys Ser Phe Lys Val Thr Thr Ser Ile
145                 150                 155                 160

Arg Asn Lys Met Gln Lys Glu Tyr Ala Leu Phe Tyr Lys Leu Asp Val
                165                 170                 175

Val Pro Ile Asp Asn Asp Asn Thr Ser Tyr Lys Leu Ile Asn Cys Asn
            180                 185                 190

Thr Ser Val Ile Thr Gln Ala Cys Pro Lys Val Ser Phe Glu Pro Ile
        195                 200                 205

Pro Ile His Tyr Cys Ala Pro Ala Gly Phe Ala Ile Leu Lys Cys Asn
210 215 220

Asp Lys Lys Phe Asn Gly Ser Gly Pro Cys Thr Asn Val Ser Thr Val
225 230 235 240

Gln Cys Thr His Gly Ile Arg Pro Val Val Ser Thr Gln Leu Leu Leu
245 250 255

Asn Gly Ser Leu Ala Glu Glu Gly Val Val Ile Arg Ser Glu Asn Phe
260 265 270

Thr Asp Asn Ala Lys Thr Ile Ile Val Gln Leu Lys Glu Ser Val Glu
275 280 285

Ile Asn Cys Thr Arg Pro Asn Asn Asn Thr Arg Lys Ser Ile Thr Ile
290 295 300

Gly Pro Gly Arg Ala Phe Tyr Ala Thr Gly Asp Ile Ile Gly Asp Ile
305 310 315 320

Arg Gln Ala His Cys Asn Ile Ser Gly Glu Lys Trp Asn Asn Thr Leu
325 330 335

Lys Gln Ile Val Thr Lys Leu Gln Ala Gln Phe Gly Asn Lys Thr Ile
340 345 350

Val Phe Lys Gln Ser Ser Gly Gly Asp Pro Glu Ile Val Met His Ser
355 360 365

Phe Asn Cys Gly Gly Glu Phe Phe Tyr Cys Asn Ser Thr Gln Leu Phe
370 375 380

Asn Ser Thr Trp Asn Asn Thr Ile Gly Pro Asn Asn Thr Asn Gly Thr
385 390 395 400

Ile Thr Leu Pro Cys Arg Ile Lys Gln Ile Ile Asn Arg Trp Gln Glu
405 410 415

Val Gly Lys Ala Met Tyr Ala Pro Pro Ile Arg Gly Gln Ile Arg Cys
420 425 430

Ser Ser Asn Ile Thr Gly Leu Leu Leu Thr Arg Asp Gly Gly Lys Glu
435 440 445

Ile Ser Asn Thr Thr Glu Ile Phe Arg Pro Gly Gly Gly Asp Met Arg
450 455 460

Asp Asn Trp Arg Ser Glu Leu Tyr Lys Tyr Lys Val Val Lys Ile Glu
465 470 475 480

Pro Leu Gly Val Ala Pro Thr Lys Ala Lys Arg Arg Val Val Gln Arg
485 490 495

Glu Lys Arg

<210> SEQ ID NO 6
<211> LENGTH: 855
<212> TYPE: PRT
<213> ORGANISM: Artificial Sequence
<220> FEATURE:
<223> OTHER INFORMATION: Env polypeptide precursor of SF2 strain

<400> SEQUENCE: 6

Met Lys Val Lys Gly Thr Arg Arg Asn Tyr Gln His Leu Trp Arg Trp
1 5 10 15

Gly Thr Leu Leu Leu Gly Met Leu Met Ile Cys Ser Ala Thr Glu Lys
20 25 30

Leu Trp Val Thr Val Tyr Tyr Gly Val Pro Val Trp Lys Glu Ala Thr
35 40 45

Thr Thr Leu Phe Cys Ala Ser Asp Ala Arg Ala Tyr Asp Thr Glu Val
50 55 60

His Asn Val Trp Ala Thr His Ala Cys Val Pro Thr Asp Pro Asn Pro
65 70 75 80

-continued

```
Gln Glu Val Val Leu Gly Asn Val Thr Glu Asn Phe Asn Met Trp Lys
                85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Leu Gly Lys Ala Thr Asn Thr Asn Ser Ser Asn Trp
    130                 135                 140

Lys Glu Glu Ile Lys Gly Glu Ile Lys Asn Cys Ser Phe Asn Ile Thr
145                 150                 155                 160

Thr Ser Ile Arg Asp Lys Ile Gln Lys Glu Asn Ala Leu Phe Arg Asn
                165                 170                 175

Leu Asp Val Val Pro Ile Asp Asn Ala Ser Thr Thr Thr Asn Tyr Thr
            180                 185                 190

Asn Tyr Arg Leu Ile His Cys Asn Arg Ser Val Ile Thr Gln Ala Cys
        195                 200                 205

Pro Lys Val Ser Phe Glu Pro Ile Pro Ile His Tyr Cys Thr Pro Ala
    210                 215                 220

Gly Phe Ala Ile Leu Lys Cys Asn Asn Lys Thr Phe Asn Gly Lys Gly
225                 230                 235                 240

Pro Cys Thr Asn Val Ser Thr Val Gln Cys Thr His Gly Ile Arg Pro
                245                 250                 255

Ile Val Ser Thr Gln Leu Leu Leu Asn Gly Ser Leu Ala Glu Glu Glu
            260                 265                 270

Val Val Ile Arg Ser Asp Asn Phe Thr Asn Asn Ala Lys Thr Ile Ile
        275                 280                 285

Val Gln Leu Asn Glu Ser Val Ala Ile Asn Cys Thr Arg Pro Asn Asn
    290                 295                 300

Asn Thr Arg Lys Ser Ile Tyr Ile Gly Pro Gly Arg Ala Phe His Thr
305                 310                 315                 320

Thr Gly Arg Ile Ile Gly Asp Ile Arg Lys Ala His Cys Asn Ile Ser
                325                 330                 335

Arg Ala Gln Trp Asn Asn Thr Leu Glu Gln Ile Val Lys Lys Leu Arg
            340                 345                 350

Glu Gln Phe Gly Asn Asn Lys Thr Ile Val Phe Asn Gln Ser Ser Gly
        355                 360                 365

Gly Asp Pro Glu Ile Val Met His Ser Phe Asn Cys Arg Gly Glu Phe
    370                 375                 380

Phe Tyr Cys Asn Thr Thr Gln Leu Phe Asn Asn Thr Trp Arg Leu Asn
385                 390                 395                 400

His Thr Glu Gly Thr Lys Gly Asn Asp Thr Ile Ile Leu Pro Cys Arg
                405                 410                 415

Ile Lys Gln Ile Ile Asn Met Trp Gln Glu Val Gly Lys Ala Met Tyr
            420                 425                 430

Ala Pro Pro Ile Gly Gly Gln Ile Ser Cys Ser Ser Asn Ile Thr Gly
        435                 440                 445

Leu Leu Leu Thr Arg Asp Gly Gly Thr Asn Val Thr Asn Asp Thr Glu
    450                 455                 460

Val Phe Arg Pro Gly Gly Gly Asp Met Arg Asp Asn Trp Arg Ser Glu
465                 470                 475                 480

Leu Tyr Lys Tyr Lys Val Ile Lys Ile Glu Pro Leu Gly Ile Ala Pro
                485                 490                 495

Thr Lys Ala Lys Arg Arg Val Val Gln Arg Glu Lys Arg Ala Val Gly
            500                 505                 510
```

-continued

```
Ile Val Gly Ala Met Phe Leu Gly Phe Leu Gly Ala Ala Gly Ser Thr
        515                 520                 525

Met Gly Ala Val Ser Leu Thr Leu Thr Val Gln Ala Arg Gln Leu Leu
    530                 535                 540

Ser Gly Ile Val Gln Gln Gln Asn Asn Leu Leu Arg Ala Ile Glu Ala
545                 550                 555                 560

Gln Gln His Leu Leu Gln Leu Thr Val Trp Gly Ile Lys Gln Leu Gln
                565                 570                 575

Ala Arg Val Leu Ala Val Glu Arg Tyr Leu Arg Asp Gln Gln Leu Leu
            580                 585                 590

Gly Ile Trp Gly Cys Ser Gly Lys Leu Ile Cys Thr Thr Ala Val Pro
        595                 600                 605

Trp Asn Ala Ser Trp Ser Asn Lys Ser Leu Glu Asp Ile Trp Asp Asn
    610                 615                 620

Met Thr Trp Met Gln Trp Glu Arg Glu Ile Asp Asn Tyr Thr Asn Thr
625                 630                 635                 640

Ile Tyr Thr Leu Leu Glu Glu Ser Gln Asn Gln Gln Glu Lys Asn Glu
                645                 650                 655

Gln Glu Leu Leu Glu Leu Asp Lys Trp Ala Ser Leu Trp Asn Trp Phe
            660                 665                 670

Ser Ile Thr Asn Trp Leu Trp Tyr Ile Lys Ile Phe Ile Met Ile Val
        675                 680                 685

Gly Gly Leu Val Gly Leu Arg Ile Val Phe Ala Val Leu Ser Ile Val
    690                 695                 700

Asn Arg Val Arg Gln Gly Tyr Ser Pro Leu Ser Phe Gln Thr Arg Leu
705                 710                 715                 720

Pro Val Pro Arg Gly Pro Asp Arg Pro Asp Gly Ile Glu Glu Glu Gly
                725                 730                 735

Gly Glu Arg Asp Arg Asp Arg Ser Val Arg Leu Val Asp Gly Phe Leu
            740                 745                 750

Ala Leu Ile Trp Glu Asp Leu Arg Ser Leu Cys Leu Phe Ser Tyr Arg
        755                 760                 765

Arg Leu Arg Asp Leu Leu Leu Ile Ala Ala Arg Thr Val Glu Ile Leu
    770                 775                 780

Gly His Arg Gly Trp Glu Ala Leu Lys Tyr Trp Trp Ser Leu Leu Gln
785                 790                 795                 800

Tyr Trp Ile Gln Glu Leu Lys Asn Ser Ala Val Ser Trp Leu Asn Ala
                805                 810                 815

Thr Ala Ile Ala Val Thr Glu Gly Thr Asp Arg Val Ile Glu Val Ala
            820                 825                 830

Gln Arg Ala Tyr Arg Ala Ile Leu His Ile His Arg Arg Ile Arg Gln
        835                 840                 845

Gly Leu Glu Arg Leu Leu Leu
    850                 855


<210> SEQ ID NO 7
<211> LENGTH: 31
<212> TYPE: PRT
<213> ORGANISM: Artificial Sequence
<220> FEATURE:
<223> OTHER INFORMATION: Amino acid alignment of CDR2-like loop
<220> FEATURE:
<221> NAME/KEY: MISC_FEATURE
<222> LOCATION: (1)..(1)
<223> OTHER INFORMATION: Xaa = Ala in scyllatoxin. Xaa is not present
      in hCD4, CD4M3, CD4M8 and CD4M9
```

-continued

```
<220> FEATURE:
<221> NAME/KEY: MISC_FEATURE
<222> LOCATION: (2)..(2)
<223> OTHER INFORMATION: Xaa = Phe in scyllatoxin. Xaa is not present
      in hCD4, CD4M3, CD4M8 and CD4M9
<220> FEATURE:
<221> NAME/KEY: MISC_FEATURE
<222> LOCATION: (3)..(3)
<223> OTHER INFORMATION: Xaa = Cys in scyllatoxin, CD4M3, CD4M8 and
      CD4M9. Xaa is not present in hCD4
<220> FEATURE:
<221> NAME/KEY: MISC_FEATURE
<222> LOCATION: (4)..(4)
<223> OTHER INFORMATION: Xaa = Asn in scyllatoxin, CD4M3, CD4M8 and
      CD4M9. Xaa is not present in hCD4
<220> FEATURE:
<221> NAME/KEY: MISC_FEATURE
<222> LOCATION: (5)..(5)
<223> OTHER INFORMATION: Xaa = Leu in scyllatoxin, CD4M3, CD4M8 and
      CD4M9. Xaa is not present in hCD4
<220> FEATURE:
<221> NAME/KEY: MISC_FEATURE
<222> LOCATION: (6)..(6)
<223> OTHER INFORMATION: Xaa = Arg in scyllatoxin. Xaa = Ala in CD4M3,
      CD4M8 and CD4M9. Xaa is not present in hCD4
<220> FEATURE:
<221> NAME/KEY: MISC_FEATURE
<222> LOCATION: (7)..(7)
<223> OTHER INFORMATION: Xaa = Met in scyllatoxin. Xaa = Arg in CD4M3,
      CD4M8 and CD4M9. Xaa is not present in hCD4
<220> FEATURE:
<221> NAME/KEY: MISC_FEATURE
<222> LOCATION: (8)..(8)
<223> OTHER INFORMATION: Xaa = Cys in scyllatoxin, CD4M3, CD4M8 and
      CD4M9. Xaa is not present in hCD4
<220> FEATURE:
<221> NAME/KEY: MISC_FEATURE
<222> LOCATION: (9)..(9)
<223> OTHER INFORMATION: Xaa = Gln in scyllatoxin, CD4M3, CD4M8 and
      CD4M9. Xaa is not present in hCD4
<220> FEATURE:
<221> NAME/KEY: MISC_FEATURE
<222> LOCATION: (10)..(10)
<223> OTHER INFORMATION: Xaa = Leu in scyllatoxin, CD4M3, CD4M8 and
      CD4M9. Xaa is not present in hCD4
<220> FEATURE:
<221> NAME/KEY: MISC_FEATURE
<222> LOCATION: (11)..(11)
<223> OTHER INFORMATION: Xaa = Ser in scyllatoxin, CD4M3 and CD4M8.
      Xaa = Arg in CD4M9. Xaa is not present in hCD4
<220> FEATURE:
<221> NAME/KEY: MISC_FEATURE
<222> LOCATION: (12)..(12)
<223> OTHER INFORMATION: Xaa = Cys in scyllatoxin, CD4M3, CD4M8 and
      CD4M9. Xaa is not present in hCD4
<220> FEATURE:
<221> NAME/KEY: MISC_FEATURE
<222> LOCATION: (13)..(13)
<223> OTHER INFORMATION: Xaa = Arg in scyllatoxin. Xaa = Lys in CD4M3,
      CD4M8 and CD4M9. Xaa is not present in hCD4
<220> FEATURE:
<221> NAME/KEY: MISC_FEATURE
<222> LOCATION: (14)..(14)
<223> OTHER INFORMATION: Xaa = Ser in scyllatoxin, CD4M3, CD4M8 and
      CD4M9. Xaa is not present in hCD4
<220> FEATURE:
<221> NAME/KEY: MISC_FEATURE
<222> LOCATION: (15)..(15)
<223> OTHER INFORMATION: Xaa = Gln in hCD4. Xaa = Leu in scyllatoxin,
      CD4M3, CD4M8 and CD4M9
<220> FEATURE:
<221> NAME/KEY: MISC_FEATURE
<222> LOCATION: (16)..(16)
<223> OTHER INFORMATION: Xaa = Ile in hCD4. Xaa = Gly in scyllatoxin,
      CD4M3, CD4M8 and CD4M9
<220> FEATURE:
<221> NAME/KEY: MISC_FEATURE
<222> LOCATION: (17)..(17)
<223> OTHER INFORMATION: Xaa = Lys in hCD4. Xaa = Leu in scyllatoxin,
      CD4M3, CD4M8 and CD4M9
```

```
<220> FEATURE:
<221> NAME/KEY: MISC_FEATURE
<222> LOCATION: (18)..(18)
<223> OTHER INFORMATION: Xaa = Ile in hCD4. Xaa = Leu in scyllatoxin and
      CD4M9. Xaa = Lys in CD4M3 and CD4M8
<220> FEATURE:
<221> NAME/KEY: MISC_FEATURE
<222> LOCATION: (19)..(19)
<223> OTHER INFORMATION: Xaa = Leu in hCD4. Xaa = Gly in scyllatoxin,
      CD4M3, CD4M8 and CD4M9
<220> FEATURE:
<221> NAME/KEY: MISC_FEATURE
<222> LOCATION: (20)..(20)
<223> OTHER INFORMATION: Xaa = Gly in hCD4, CD4M3 and CD4M8. Xaa = Lys
      in scyllatoxin and CD4M9
<220> FEATURE:
<221> NAME/KEY: MISC_FEATURE
<222> LOCATION: (21)..(21)
<223> OTHER INFORMATION: Xaa = Asn in hCD4. Xaa = Cys in scyllatoxin,
      CD4M3, CD4M8 and CD4M9.
<220> FEATURE:
<221> NAME/KEY: MISC_FEATURE
<222> LOCATION: (22)..(22)
<223> OTHER INFORMATION: Xaa = Gln in hCD4 and CD4M3. Xaa = Ile in
      Scyllatoxin. Xaa = Ala in CD4M8 and CD4M9
<220> FEATURE:
<221> NAME/KEY: MISC_FEATURE
<222> LOCATION: (24)..(24)
<223> OTHER INFORMATION: Xaa = Ser in hCD4, CD4M3, CD4M8 and CD4M9.
      Xaa = Asp in Scyllatoxin.
<220> FEATURE:
<221> NAME/KEY: MISC_FEATURE
<222> LOCATION: (25)..(25)
<223> OTHER INFORMATION: Xaa = Phe in hCD4, CD4M3, CD4M8 and CD4M9.
      Xaa = Lys in Scyllatoxin.
<220> FEATURE:
<221> NAME/KEY: MISC_FEATURE
<222> LOCATION: (26)..(26)
<223> OTHER INFORMATION: Xaa = Leu in hCD4. Xaa = Cys in Scyllatoxin,
      CD4M3, CD4M8 and CD4M9.
<220> FEATURE:
<221> NAME/KEY: MISC_FEATURE
<222> LOCATION: (27)..(27)
<223> OTHER INFORMATION: Xaa = Thr in hCD4 and CD4M3. Xaa = Glu in
      Scyllatoxin. Xaa = Ala in CD4M8 and CD4M9
<220> FEATURE:
<221> NAME/KEY: MISC_FEATURE
<222> LOCATION: (28)..(28)
<223> OTHER INFORMATION: Xaa = Lys in hCD4. Xaa = Cys in Scyllatoxin,
      CD4M3, CD4M8 and CD4M9.
<220> FEATURE:
<221> NAME/KEY: MISC_FEATURE
<222> LOCATION: (29)..(29)
<223> OTHER INFORMATION: Xaa = Gly in hCD4, CD4M3, CD4M8 and CD4M9.
      Xaa = Val in Scyllatoxin.
<220> FEATURE:
<221> NAME/KEY: MISC_FEATURE
<222> LOCATION: (30)..(30)
<223> OTHER INFORMATION: Xaa = Phe in hCD4 and CD4M9. Xaa = Lys in
      Scyllatoxin. Xaa is not present in CD4M3 and CD4M8
<220> FEATURE:
<221> NAME/KEY: MISC_FEATURE
<222> LOCATION: (31)..(31)
<223> OTHER INFORMATION: Xaa = His in Scyllatoxin. Xaa is not present in
      hCD4, CD4M3, CD4M8 and CD4M9.

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Gly Xaa Xaa Xaa Xaa Xaa Xaa Xaa Xaa
            20                  25                  30
```

METHOD OF INDUCING AN ANTIVIRAL IMMUNE RESPONSE AGAINST HIV-1 UTILIZING CHIMERIC HIV ENV PROTEINS COMPRISING CD4 MINI-PROTEINS OR CD4 MIMETICS

CROSS REFERENCE TO RELATED APPLICATIONS

This application is a division of Ser. No. 12/859,356, filed on Aug. 19, 2010, now issued as U.S. Pat. No. 8,226,955, which is a division of Ser. No. 10/514,055, filed on Nov. 8, 2004, now issued as U.S. Pat. No. 7,811,580, which is the U.S. National Phase of PCT/US2003/014575, filed May 7, 2003, which claims priority to Ser. No. 60/459,314, filed Mar. 31, 2003, and Ser. No. 60/378,543, filed May 7, 2002. Each of these applications is incorporated herein by reference in its entirety.

STATEMENT REGARDING FEDERALLY SPONSORED RESEARCH OR DEVELOPMENT

The invention was supported in whole, or in part, by NIAID-NIH HIVRAD Grant No. 5P01 AI48225-03 from the National Institute of Allergy and Infectious Diseases. The Government has certain rights in the invention.

SEQUENCE LISTING

This application incorporates by reference the contents of a 24 kb text file created on Jun. 26, 2012 and named "PAT051269_US_DIV.txt," which is the sequence listing for this application.

TECHNICAL FIELD

The invention relates generally to modified HIV envelope (Env) polypeptides that are useful as immunizing agents or for generating an immune response in a subject, for example a cellular immune response or a protective immune response. More particularly, the invention relates Env polypeptides such as monomeric or oligomeric gp120, gp140 or gp160 complexed to CD4 proteins or mini-proteins wherein conserved, cryptic epitopes participating in Env-CD4 and chemokine receptor binding are exposed. The invention also pertains to methods of using these polypeptides to elicit an immune response against a broad range of HIV subtypes.

BACKGROUND OF THE INVENTION

The human immunodeficiency virus (HIV-1, also referred to as HTLV-III, LAV or HTLV-III/LAV) is the etiological agent of the acquired immune deficiency syndrome (AIDS) and related disorders. (see, e.g., Barre-Sinoussi, et al., (1983) *Science* 220:868-871; Gallo et al. (1984) *Science* 224:500-503; Levy et al., (1984) *Science* 225:840-842; Siegal et al., (1981) *N Engl. J Med.* 305:1439-1444). AIDS patients usually have a long asymptomatic period followed by the progressive degeneration of the immune system and the central nervous system. Replication of the virus is highly regulated, and both latent and lytic infection of the CD4 positive helper subset of T-lymphocytes occurs in tissue culture (Zagury et al., (1986) *Science* 231:850-853). Molecular studies of HIV-1 show that it encodes a number of genes (Ratner et al., (1985) Nature 313:277-284; Sanchez-Pescador et al., (1985) Science 227:484-492), including three structural genes—gag, pol and env—that are common to all retroviruses. Nucleotide sequences from viral genomes of other retroviruses, particularly HIV-2 and simian immunodeficiency viruses, SIV (previously referred to as STLV-III), also contain these structural genes. (Guyader et al., (1987) *Nature* 326:662-669). The envelope protein of HIV-1, HIV-2 and SIV is a glycoprotein of about 160 kd (gp160). During virus infection of the host cell, gp160 is cleaved by host cell proteases to form gp120 and the integral membrane protein, gp41. The gp41 portion is anchored in the membrane bilayer of virion, while the gp120 segment protrudes into the surrounding environment. gp120 and gp41 are more covalently associated and free gp120 can be released from the surface of virions and infected cells.

Crystallography studies of the gp120 core polypeptide indicate that this polypeptide is folded into two major domains having certain emanating structures. The inner domain (inner with respect to the N and C terminus) features a two-helix, two-stranded bundle with a small five-stranded β-sandwich at its termini-proximal end and a projection at the distal end from which the V1/V2 stem emanates. The outer domain is a staked double barrel that lies along side the inner domain so that the outer barrel and inner bundle axes are approximately parallel. Between the distal inner domain and the distal outer domain is a four-stranded bridging sheet that holds a peculiar minidomain in contact with, but distinct from, the inner, the outer domain, and the V1/V2 domain. The bridging sheet is composed of four β-strand structures (β-3, β-2, β-21, β-20). The bridging region is packed primarily over the inner domain, although some surface residues of the outer domain, such as Phe 382, reach into the bridging sheet to form part of its hydrophobic core. See, also WO 00/39303.

The basic unit of the β-sheet conformation of the bridging sheet region is the β-strand that exists as a less tightly coiled helix, with 2.0 residues per turn. The β-strand conformation is only stable when incorporated into β-sheet, where hydrogen bonds with close to optimal geometry are formed between the peptide groups on adjacent β-strands; the dipole moments of the strands are also aligned favorably. Side chains from adjacent residues of the same strand protrude from opposite sides of the sheet and do not interact with each other, but have significant interactions with their backbone and with the side chains of neighboring strands. For a general description of β-sheets, see, e.g., T. E. Creighton, *Proteins: Structures and Molecular Properties* (W.H. Freeman and Company, 1993); and A. L. Lehninger, *Biochemistry* (Worth Publishers, Inc., 1975).

The gp120 polypeptide is instrumental in mediating entry into the host cell. Recent studies have indicated that binding of CD4 to gp120 induces a conformational change in Env that allows for binding to a co-receptor (e.g., a chemokine receptor) and subsequent entry of the virus into the cell. (Wyatt, R., et al. (1998) *Nature* 393:705-711; Kwong, P., et al. (1998) *Nature* 393:648-659). It appears as though CD4 is bound into a depression formed at the interface of the outer domain, the inner domain and the bridging sheet of gp120.

Immunogenicity of the gp120 polypeptide has also been studied. For example, individuals infected by HIV-1 usually develop antibodies that can neutralize the virus in in vitro assays, and this response is directed primarily against linear neutralizing determinants in the third variable loop of gp120 glycoprotein (Javaherian, K., et al. (1989) *Proc. Natl. Acad. Sci.* 86:6786-6772; Matsushita, M., et al. (1988) *J. Virol.* 62:2107-2144; Putney, S., et al. (1986) *Science* 234:1392-1395; Rushe, J. R., et al. (1988) *Proc. Nat. Acad. Sci. USA* 85: 3198-3202). However, these antibodies generally exhibit the ability to neutralize only a limited number of HIV-1 strains (Matthews, T. (1986) *Proc. Natl. Acad. Sci. USA.* 83:9709-9713; Nara, P. L., et al. (1988) *J. Virol.* 62:2622-2628; Palker, T. J., et al. (1988) *Proc. Natl. Acad. Sci. USA.* 85:1932-1936). Later in the course of HIV infection in humans, antibodies capable of neutralizing a wider range of HIV-1 isolates appear (Barre-Sinoussi, F., et al. (1983) *Science* 220:868-871; Robert-Guroff, M., et al. (1985) *Nature* (London) 316:72-74; Weis, R., et al. (1985) *Nature* (London) 316:69-72; Weis, R., et al. (1986) *Nature* (London) 324:572-575).

Stamatatos et al (1998) *AIDS Res Hum Retroviruses* 14(13):1129-39 show that a deletion of the variable region 2 from a HIV-$1_{SF162}$ virus, which utilizes the CCR-5 co-receptor for virus entry, rendered the virus highly susceptible to serum-mediated neutralization. This V2 deleted virus was also neutralized by sera obtained from patients infected not only with Glade B HIV-1 isolates but also with Glade A, C, D and F HIV-1 isolates. However, deletion of the variable region 1 had no effect. Deletion of the variable regions 1 and 2 from a LAI isolate HIV-$I_{IIIB}$ also increased the susceptibility to neutralization by monoclonal antibodies whose epitopes are located within the V3 loop, the CD4-binding site, and conserved gp120 regions (Wyatt, R., et al. (1995) *J Virol.* 69:5723-5733). Rabbit immunogenicity studies done with the HIV-1 virus with deletions in the V1/V2 and V3 region from the LM strain, which uses the CXCR4 co-receptor for virus entry, showed no improvement in the ability of Env to raise neutralizing antibodies (Leu et al. (1998) *AIDS Res. and Human Retroviruses.* 14:151-155).

Further, a subset of the broadly reactive antibodies, found in most infected individuals, interferes with the binding of gp120 and CD4 (Kang, C.-Y., et al. (1991) *Proc. Natl. Acad. Sci. USA.* 88:6171-6175; McDougal, J. S., et al. (1986) *J. Immunol.* 137:2937-2944). Other antibodies are believed to bind to the chemokine receptor-binding region after CD4 has bound to Env (Thali et al. (1993) *J. Virol.* 67:3978-3988). The fact that neutralizing antibodies generated during the course of HIV infection do not provide permanent antiviral effect may in part be due to the generation of "neutralization escapes" virus mutants and to the general decline in the host immune system associated with pathogenesis. In contrast, the presence of pre-existing neutralizing antibodies upon initial HIV-1 exposure will likely have a protective effect.

It is widely thought that a successful vaccine should be able to induce a strong, broadly neutralizing antibody response against diverse HIV-1 strains (Montefiori and Evans (1999) *AIDS Res. Hum. Ret.* 15(8):689-698; Bolognesi, D. P., et al. (1994) *Ann. Int. Med.* 8:603-611; Haynes, B., F., et al. (1996) *Science;* 271: 324-328.). Neutralizing antibodies, by attaching to the incoming virions, can reduce or even prevent their infectivity for target cells and prevent the cell-to-cell spread of virus in tissue culture (Hu et al. (1992) *Science* 255:456-459; Burton, D., R. and Montefiori, D. (1997) *AIDS* 11(suppl. A): 587-598). However as described above, antibodies directed against gp120 do not generally exhibit broad antibody responses against different HIV strains.

Currently, the focus of vaccine development, from the perspective of humoral immunity, is on the neutralization of primary isolates that utilize the CCR5 chemokine co-receptor believed to be important in virus entry (Zhu, T., et al. (1993) *Science* 261:1179-1181; Fiore, J., et al. (1994) Virology; 204: 297-303). These viruses are generally much more resistant to antibody neutralization than T-cell line adapted strains that use the CXCR4 co-receptor, although both can be neutralized in vitro by certain broadly and potent acting monoclonal antibodies, such as IgG1b12, 2G12 and 2F5 (Trkola, A., et al. (1995) *J. Virol.* 69:6609-6617; D'Sousa P M., et al (1997) *J. Infect. Dis.* 175:1062-1075). These monoclonal antibodies are directed to the CD4 binding site, a glycosylation site and to the gp41 fusion domain, respectively.

The problem that remains, however, is that it is not known how to induce antibodies of the appropriate specificity by vaccination. Antibodies (Abs) elicited by gp120 glycoprotein from a given isolate are usually only able to neutralize closely related viruses generally from similar, usually from the same, HIV-1 subtype. Thus, there remains a need for Env antigens that can elicit an immunological response (e.g., neutralizing and/or protective antibodies) in a subject against multiple HIV strains and subtypes, for example when administered as a vaccine.

SUMMARY OF THE INVENTION

The present invention solves these and other problems by providing hybrid Env-CD4 proteins and Env polypeptides (e.g., native or modified gp120) complexed to novel, CD4 mini-proteins or mimics (mimetics) in order to expose epitopes in or near the CD4 binding site.

In one aspect, the invention includes a polynucleotide encoding a hybrid HIV Env-CD4 protein, where the protein include amino acid sequences from an HIV Env and CD4 amino acid sequences. In certain embodiments, the CD4-encoding polynucleotide sequences are inserted into (or embedded) within the HIV Env-encoding polynucleotides sequences, for example inserted in place of polynucleotides encoding for one or more amino acid residues in the variable regions (V1-V5) of HIV Env. Thus, the invention includes a polynucleotide comprising a first sequence encoding an HIV Env polypeptide and a second sequence encoding a CD4 protein, wherein the second sequence is inserted into, and in proper reading frame with, the first sequence. In certain embodiments, the HIV Env polypeptide of the hybrid is encoded by a modified gp120 sequence (SEQ ID NO:5) and the second sequence comprises one or more of SEQ ID NO:1-4. In certain embodiments, the HIV Env polypeptide is based on strain SF162. In any of the polypeptides described herein, one or more of the Env variable regions (V1-V5) regions may be modified (e.g., contain deletions and/or substitutions).

In any of the polynucleotides described herein can further comprise one or more linker sequences, for example, linker sequences flanking the CD4-encoding sequence (second sequence). Further, when any of the polynucleotides described herein are expressed, the CD4 peptide is preferably bound to (complexed) to the HIV Env polypeptide such that cryptic epitopes are exposed in the modified Env polypeptide.

In yet another aspect, the invention includes polypeptides encoding by any of the polynucleotides described herein. Thus, in certain embodiments, the polypeptide comprises a hybrid Env-CD4 protein, for example, a hybrid polypeptide comprising an Env polypeptide (e.g., native or modified gp160, gp140, oligomeric-gp140, gp120) and a CD4 protein (e.g., sCD4, CD4 mimetics, CD4 mini-proteins such as SEQ ID NO:1-4, etc.). The Env polypeptide may include one or more modifications, for example deletions in one or more of the variable regions. In certain embodiments, the CD4 protein is inserted into the Env polypeptide, for example into one of the deletions.

In yet another aspect, the invention includes polypeptide complexes comprising an HIV Env polypeptide (e.g., native or modified gp160, gp140, oligomeric-gp140, gp120) complexed to a CD4 protein (e.g., sCD4, CD4 mimetics, CD4 mini-proteins such as SEQ ID NO:1-4, etc.). The HIV Env polypeptide and CD4 protein can be complexed by crosslinking (e.g., using formaldehyde); using a fixative (e.g., formalin); and/or can complex spontaneously to form a covalent bond under suitable conditions. Polynucleotides encoding the components of the complex are also described herein, for example one or more polynucleotide encoding both the Env and CD4 polypeptides (e.g., soluble CD4) can be expressed and the resulting proteins complexed together.

In yet another aspect, the invention includes immunogenic compositions comprising any of the polynucleotides and/or polypeptides described herein. In certain embodiments, the immunogenic compositions further comprise one or more adjuvants.

In a still further aspect, the invention includes a cell comprising any of the polynucleotides and/or polypeptides described herein. The polynucleotide sequences are preferably operably linked to control elements compatible with expression in the selected cell. The cell can be, for example, a mammalian cell. (e.g., BHK, VERO, HT1080, 293, RD, COS-7, and CHO cells); an insect cell (e.g., *Trichoplusia ni* (Tn5) or Sf9 cells); a bacterial cell; a yeast cell; a plant cell; an antigen presenting cell; a lymphoid cell selected from the group consisting of macrophage, monocytes, dendritic cells, B-cells, T-cells, stem cells, and progenitor cells thereof; a primary cell; an immortalized cell; and/or a tumor-derived cell.

In another aspects, the invention includes a gene delivery vector for use in a mammalian subject, comprising a suitable gene delivery vector for use in said subject, wherein the vector comprises any of the polynucleotides described herein operably linked to control elements compatible with expression in the subject.

In yet another aspect, the invention includes a method of producing antibodies that bind to cryptic epitopes of HIV Env. In certain embodiments, the methods comprising the step of administering any of the polypeptides described herein to a subject under conditions that allow production of antibodies. In other embodiments, epitopes involved in neutralization of HIV are identified, for example by identifying an epitope (e.g., determining the sequence of epitope) and antibodies produced by administering the identified epitope(s) to a subject under conditions that allow production of antibodies. The invention also includes antibodies produced by any of the methods described herein. In any of the methods and compositions described herein, the antibodies can be neutralizing antibodies, monoclonal antibodies and/or polyclonal antibodies). In certain embodiments, the antibodies produced in the subject are then isolated.

In a still further aspect, the invention includes a method for producing a hybrid Env-CD4 polypeptide comprising incubating any of the cells described herein, under conditions suitable for producing said polypeptide In yet another aspect, the invention includes a method of inducing an immune response (e.g., a humoral response such as a neutralizing antibody response and/or a cellular immune response) in subject comprising, administering any of the polynucleotides, to polypeptides and/or immunogenic compositions described herein to a subject in an amount sufficient to induce an immune response in the subject. In certain embodiments, the method comprises transfecting cells ex vivo and reintroducing the transfected cells into the subject. In other embodiments, the method includes DNA immunization of a subject, for example, by introducing any of the polynucleotides and/or gene delivery vectors described herein into said subject under conditions that are compatible with expression of said expression cassette and production of a polypeptide in said subject. In other embodiments, the methods comprise (a) administering a first composition comprising any of the polynucleotides described herein in a priming step and (b) administering a second composition comprising any of the polypeptides described herein, as a booster, in an amount sufficient to induce an immune response in the subject. In any of the methods described herein, the vectors may comprise non-viral vectors or viral vectors such as retroviral (e.g., lentiviral) vectors. Further, the polynucleotides and/or vector may be introduced, for example, using a particulate carrier (e.g., coated on a gold or tungsten particle and said coated particle is delivered to said subject using a gene gun) or encapsulated in a liposome preparation. In any of the methods described herein, the subject can be a mammal, for example a human or non-human mammal and the introduction can be intramuscularly, intramucosally, intranasally, subcutaneously, intradermally, transdermally, intravaginally, intrarectally, orally and/or intravenously.

These and other embodiments of the subject invention will readily occur to those of skill in the art in light of the disclosure herein.

BRIEF DESCRIPTION OF THE DRAWINGS

FIG. 1 (SEQ ID NO:6) depicts the primary amino acid sequence of the Env polypeptide precursor of HIV-$1_{SF2}$ (hereinafter "SF2") strain (See, also GenBank Accession No. VCLJA2 and Sanchez-Pescador et al. (1984) *Science* 227: 484).

FIG. 2 (SEQ ID NO:7) depicts amino acid sequence alignment of CDR2-like loop of human CD4, scorpion scyllatoxin, engineered CD4 mimetic (CD4M3), double (CD4M8) and quintuple (CD4M9) mutants.

FIG. 7 (SEQ ID NO:5) depicts the amino acid sequence of an HIV gp120 polypeptide encoded by a modified gp120-encoding polynucleotide sequence (gp120.modSF62). The V1 Loop is underlined; the V2 Loop is shown in bold; the V3 Loop is shown in italics; the V4 Loop is shown in dashed underlining; and the V5 Loop is shown in double underlining.

DETAILED DESCRIPTION OF THE INVENTION

Figure 3:
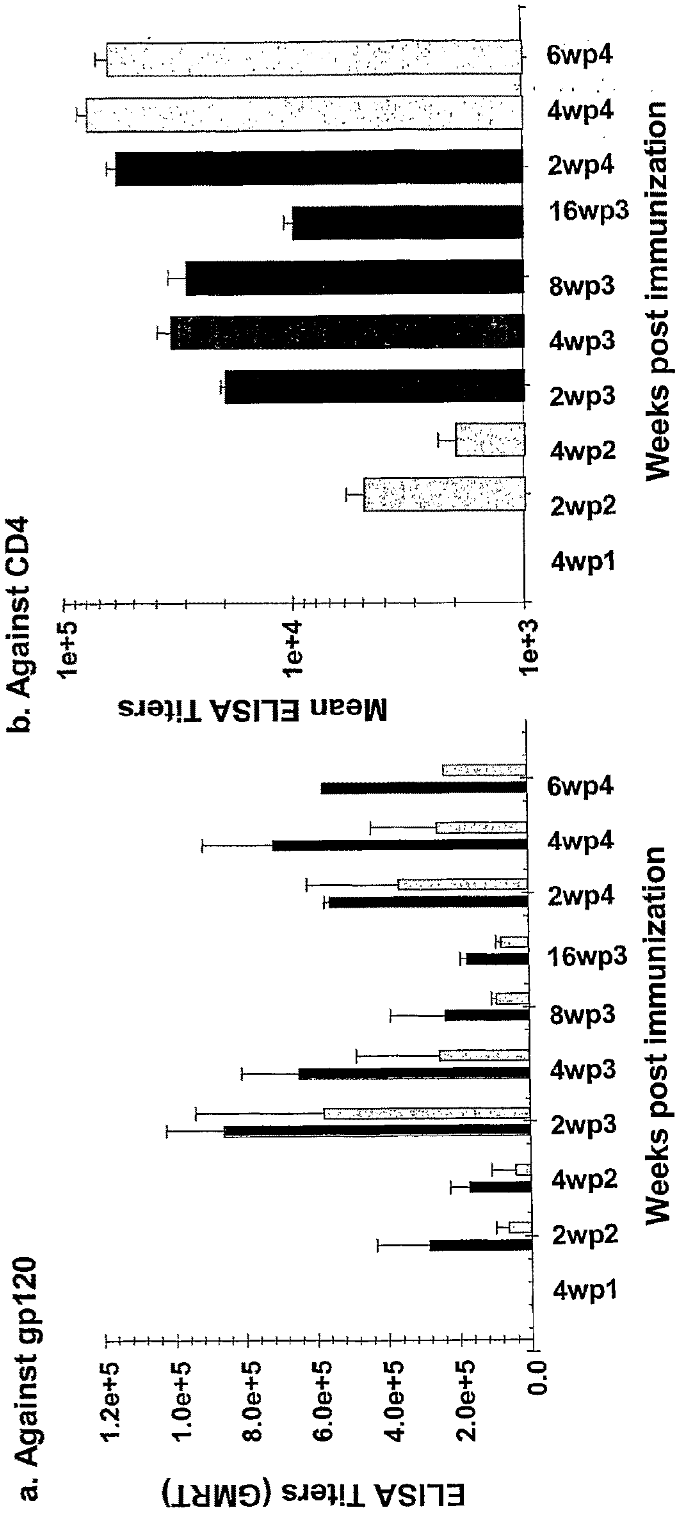
FIG. 3, panels a and b, are graphs depicting immunogenicity of gp120-sCD4 complexes. Panel a depicts antibody responses to gp120 induced by fixed (formalin or formaldehyde) and unfixed 120-sCD4 at different time points. The black bars show fixed complexes and the gray bars show unfixed complexes. Panel b shows antibody responses to CD4 (pooled specimens).

The practice of the present invention will employ, unless otherwise indicated, conventional methods of protein chemistry, viral immunobiology, molecular biology and recombinant DNA techniques within the skill of the art. Such techniques are explained fully in the literature. See, e.g., T. E. Creighton, *Proteins: Structures and Molecular Properties* (W.H. Freeman and Company, 1993); Nelson L. M. and Jerome H. K. *HIV Protocols* in Methods in Molecular Medicine, vol. 17, 1999; Sambrook, et al., *Molecular Cloning: A Laboratory Manual* (Cold Spring Harbor Laboratory, 1989); F. M. Ausubel et al. *Current Protocols in Molecular Biology*, Greene Publishing Associates & Wiley Interscience New York; and Lipkowitz and Boyd, *Reviews in Computational Chemistry*, volumes 1-present (Wiley-VCH, New York, N.Y., 1999).

It must be noted that, as used in this specification and the appended claims, the singular forms "a", "an" and "the" include plural referents unless the content clearly dictates otherwise. Thus, for example, reference to "a polypeptide" includes a mixture of two or more polypeptides, and the like.

All publications, patents and patent applications cited herein, whether supra or infra, are hereby incorporated by reference in their entirety.

DEFINITIONS

In describing the present invention, the following terms will be employed, and are intended to be defined as indicated below.

The terms "polypeptide," and "protein" are used interchangeably herein to denote any polymer of amino acid residues. The terms encompass peptides, oligopeptides, dimers, multimers, and the like. Such polypeptides can be derived from natural sources or can be synthesized or recombinantly produced. The terms also include postexpression modifications of the polypeptide, for example, glycosylation, acetylation, phosphorylation, etc.

A polypeptide as defined herein is generally made up of the 20 natural amino acids Ala (A), Arg (R), Asn (N), Asp (D), Cys (C), Gln (Q), Glu (E), Gly (G), His (H), Ile (I), Leu (L), Lys (K), Met (M), Phe (F), Pro (P), Ser (S), Thr (T), Trp (W), Tyr (Y) and Val (V) and may also include any of the several known amino acid analogs, both naturally occurring and synthesized analogs, such as but not limited to homoisoleucine, asaleucine, 2-(methylenecyclopropyl)glycine, S-methylcysteine, S-(prop-1-enyl)cysteine, homoserine, ornithine, norleucine, norvaline, homoarginine, 3-(3-carboxyphenyl)alanine, cyclohexylalanine, mimosine, pipecolic acid, 4-methylglutamic acid, canavanine, 2,3-diaminopropionic acid, and the like. Further examples of polypeptide agents that will find use in the present invention are set forth below.

By "geometry" or "tertiary structure" of a polypeptide or protein is meant the overall 3-D configuration of the protein. As described herein, the geometry can be determined, for example, by crystallography studies or by using various programs or algorithms that predict the geometry based on interactions between the amino acids making up the primary and secondary structures.

By "wild type" polypeptide, polypeptide agent or polypeptide drug, is meant a naturally occurring polypeptide sequence, and its corresponding secondary structure. An "isolated" or "purified" protein or polypeptide is a protein that is separate and discrete from a whole organism with which the protein is normally associated in nature. It is apparent that the term denotes proteins of various levels of purity. Typically, a composition containing a purified protein will be one in which at least about 35%, preferably at least about 40-50%, more preferably, at least about 75-85%, and most preferably at least about 90% or more, of the total protein in the composition will be the protein in question.

The terms "CD4 mini-protein" and "mini CD4 protein" are used interchangeably to refer to any polypeptide that interacts with Env (e.g., gp120), preferably such that epitopes (e.g., cryptic epitopes) in or near the CD4 and/or chemokine receptor binding sites(s) are exposed. Thus, a CD mini-protein can be a less than full-length fragment of CD4. In addition, the term encompasses functional and structural homologs of CD4 fragments, i.e., polypeptides that expose the cryptic epitopes on an Env protein.

By "Env polypeptide" is meant a molecule derived from an envelope protein, preferably from HIV Env. The envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides. Env polypeptides can exist as monomers, dimers or multimers.

By a "gp120 polypeptide" is meant a molecule derived from a gp120 region of the Env polypeptide. Preferably, the gp120 polypeptide is derived from HIV Env. The primary amino acid sequence of gp120 is approximately 511 amino acids, with a polypeptide core of about 60,000 Daltons. The polypeptide is extensively modified by N-linked glycosylation to increase the apparent molecular weight of the molecule to 120,000 Daltons. The amino acid sequence of gp120 contains five relatively conserved domains interspersed with five hypervariable domains. The positions of the 18 cysteine residues in the gp120 primary sequence of the HIV-$1_{HXB-2}$ (hereinafter "HXB-2") strain, and the positions of 13 of the approximately 24 N-linked glycosylation sites in the gp120 sequence are common to most, if not all, gp120 sequences. The hypervariable domains contain extensive amino acid substitutions, insertions and deletions. Despite this variation, most, if not all, gp120 sequences preserve the virus's ability to bind to the viral receptor CD4. A "gp120 polypeptide" includes both single subunits and/or multimers.

Env polypeptides (e.g., gp120, gp140 and gp160) include a "bridging sheet" comprised of 4 anti-parallel β-strands (β-2, β-3, β-20 and β-21) that form a β-sheet. Extruding from one pair of the β-strands (β-2 and β-3) are two loops, V1 and V2. The β-2 sheet occurs at approximately amino acid residue 119 (Cys) to amino acid residue 123 (Thr) while β-3 occurs at approximately amino acid residue 199 (Ser) to amino acid residue 201 (Ile), relative to HXB-2. The "V1/V2 region" occurs at approximately amino acid positions 126 (Cys) to residue 196 (Cys), relative to HXB-2. (see, e.g., Wyatt et al. (1995) *J. Virol.* 69:5723-5733; Stamatatos et al. (1998) *J. Virol.* 72:7840-7845). Extruding from the second pair of β-strands (β-20 and β-21) is a "small-loop" structure, also referred to herein as "the bridging sheet small loop." In HXB-2, β-20 extends from about amino acid residue 422 (Gln) to amino acid residue 426 (Met) while β-21 extends from about amino acid residue 430 (Val) to amino acid residue 435 (Tyr). In variant SF162, the Met-426 is an Arg (R) residue. The "small loop" extends from about amino acid residue 427 (Trp) through 429 (Lys), relative to HXB-2. Alignment of the amino acid sequences of Env polypeptide gp160 of any HIV variant can be determined relative to other variants, such as HXB-2, as described for example, in WO 00/39303.

Furthermore, an "Env polypeptide" or "gp120 polypeptide" as defined herein is not limited to a polypeptide having the exact sequence described herein. Indeed, the HIV genome is in a state of constant flux and contains several variable domains that exhibit relatively high degrees of variability between isolates. It is readily apparent that the terms encompass Env (e.g., gp120) polypeptides from any of the identified HIV isolates, as well as newly identified isolates, and subtypes of these isolates. Descriptions of structural features are given herein with reference to HXB-2. One of ordinary skill in the art in view of the teachings of the present disclosure and the art can determine corresponding regions in other HIV variants (e.g., isolates $HIV_{IIIb}$, $HIV_{SF2}$, HIV-$1_{SF162}$, HIV-$1_{SF170}$, $HIV_{LAV}$, $HIV_{LAI}$, $HIV_{MN}$, HIV-$1_{CM235}$, HIV-$1_{US4}$, other HIV-1 strains from diverse subtypes (e.g., subtypes, A through G, and O), HIV-2 strains and diverse subtypes (e.g., HIV-$2_{UC1}$ and HIV-$2_{UC2}$), and simian immunodeficiency virus (SIV). (See, e.g., Virology, 3rd Edition (W. K. Joklik ed. 1988); *Fundamental Virology,* 2nd Edition (B. N. Fields and D. M. Knipe, eds. 1991); *Virology,* 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify β-sheet regions). The actual amino acid sequences of the modified Env polypeptides can be based on any HIV variant.

Additionally, the term "Env polypeptide" (e.g., "gp120 polypeptide") encompasses proteins that include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes, such capability must be retained.

Thus, a "modified Env polypeptide" is an Env polypeptide (e.g., gp120 as defined above), which has been complexed to a CD4 mini protein and, optionally, modified in the variable regions V1 and V2. The Env polypeptide may be monomeric or oligomeric. Generally, complexed Env (e.g., gp120) polypeptides result in exposure of epitopes in or near the CD4 binding site, while allowing correct folding (e.g., correct geometry) of the Env polypeptide. Additionally, modifications (e.g., truncations) to the variable loop regions (V1, V2, V3, V4 and/or V5) may also be made. Although not all possible variable region modifications have been exemplified herein, it is to be understood that other disrupting modifications are also encompassed by the present invention.

The term "hybrid" protein, when used in reference to Env-CD4 hybrid proteins, refers to polypeptides in which CD4 amino acid sequences (e.g., mini proteins, mimetics, etc.) are inserted into (flanked by) Env amino acid sequences. Non-limiting examples of Env-CD4 hybrids are described in Example 4 in which various CD4 mini protein sequences are inserted in place of (substituted for) one or more of the variable loop regions (V1-V5) of an Env protein.

Normally, hybrid or modified polypeptides as described herein capable of secretion into growth medium in which an organism expressing the protein is cultured. However, for purposes of the present invention, such polypeptides may also be recovered intracellularly. Secretion into growth media is readily determined using a number of detection techniques, including, e.g., polyacrylamide gel electrophoresis and the like, and immunological techniques such as Western blotting and immunoprecipitation assays as described in, e.g., International Publication No. WO 96/04301.

A polypeptide is produced "intracellularly" when it is found within the cell, either associated with components of the cell, such as in association with the endoplasmic reticulum (ER) or the Golgi Apparatus, or when it is present in the soluble cellular fraction. The Env, CD4 and hybrid polypeptides of the present invention may also be secreted into growth medium so long as sufficient amounts of the polypeptides remain present within the cell such that they can be purified from cell lysates using techniques described herein.

An "immunogenic" protein is a molecule that includes at least one epitope such that the molecule is capable of either eliciting an immunological reaction in an individual to which the protein is administered or, in the diagnostic context, is capable of reacting with antibodies directed against the HIV in question.

By "epitope" is meant a site on an antigen to which specific B cells and/or T cells respond, rendering the molecule including such an epitope capable of eliciting an immunological reaction or capable of reacting with HIV antibodies present in a biological sample. The term is also used interchangeably with "antigenic determinant" or "antigenic determinant site." An epitope can comprise 3 or more amino acids in a spatial conformation unique to the epitope. Generally, an epitope consists of at least 5 such amino acids and, more usually, consists of at least 8-10 such amino acids. Methods of determining spatial conformation of amino acids are known in the art and include, for example, x-ray crystallography and 2-dimensional nuclear magnetic resonance. Furthermore, the identification of epitopes in a given protein is readily accomplished using techniques well known in the art, such as by the use of hydrophobicity studies and by site-directed serology. See, also, Geysen et al., *Proc. Natl. Acad. Sci. USA* (1984) 81:3998-4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al., *Molecular Immunology* (1986) 23:709-715 (technique for identifying peptides with high affinity for a given antibody). Antibodies that recognize the same epitope can be identified in a simple immunoassay showing the ability of one antibody to block the binding of another antibody to a target antigen. A "cryptic epitope" refers generally to an epitope that is exposed only in certain conformations of the protein.

An "immunological response" or "immune response" as used herein is the development in the subject of a humoral and/or a cellular immune response to the Env (e.g., gp120) polypeptide when the polypeptide is present in a vaccine composition. These antibodies may also neutralize infectivity, and/or mediate antibody-complement or antibody dependent cell cytotoxicity to provide protection to an immunized host. Immunological reactivity may be determined in standard immunoassays, such as a competition assays, well known in the art.

"Gene transfer" or "gene delivery" refers to methods or systems for reliably inserting DNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from alphaviruses, pox viruses and vaccinia viruses. When used for immunization, such gene delivery expression vectors may be referred to as vaccines or vaccine vectors.

The term "antibody" as used herein includes antibodies obtained from both polyclonal and monoclonal preparations, as well as, the following: (i) hybrid (chimeric) antibody molecules (see, for example, Winter et al. (1991) *Nature* 349:293-299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); and, (vii) any functional fragments obtained from such molecules, wherein such fragments retain specific-binding properties of the parent antibody molecule.

Thus, the term "antibody" refers to a polypeptide or group of polypeptides that comprise at least one antigen binding site. An "antigen binding site" is formed from the folding of the variable domains of an antibody molecule(s) to form three-dimensional binding sites with an internal surface shape and charge distribution complementary to the features of an epitope of an antigen, which allows specific binding to form an antibody-antigen complex. An antigen binding site may be formed from a heavy- and/or light-chain domain (VH and VL, respectively), which form hypervariable loops that contribute to antigen binding. The term "antibody" includes, without limitation, polyclonal antibodies, monoclonal antibodies, chimeric antibodies, altered antibodies, univalent antibodies, Fab proteins, and single-domain antibodies. In many cases, the binding phenomena of antibodies to antigens is equivalent to other ligand/anti-ligand binding.

If polyclonal antibodies are desired, a selected mammal (e.g., mouse, rabbit, goat, horse, etc.) is immunized with an immunogenic polypeptide epitope(s). Serum from the immunized animal is collected and treated according to known procedures. If serum containing polyclonal antibodies to Env-CD4 complexes and/or hybrids contain antibodies to other antigens, the polyclonal antibodies can be purified by immunoaffinity chromatography. Techniques for producing and processing polyclonal antisera are known in the art, see for example, Mayer and Walker, eds. (1987) IMMUNOCHEMICAL METHODS IN CELL AND MOLECULAR BIOLOGY (Academic Press, London).

One skilled in the art can also readily produce monoclonal antibodies directed against epitopes exposed from Env-CD4 complexes and hybrids. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al. (1980) HYBRIDOMA TECHNIQUES; Hammerling et al. (1981), MONOCLONAL ANTIBODIES AND T-CELL HYBRIDOMAS; Kennett et al. (1980) MONOCLONAL ANTIBODIES; see also, U.S. Pat. Nos. 4,341,761; 4,399,121; 4,427,783; 4,444,887; 4,466,917; 4,472,500; 4,491,632; and 4,493,890. Panels of monoclonal antibodies can be screened for various properties; i.e., for isotype, epitope affinity, etc. As used herein, a "single domain antibody" (dAb) is an antibody that is comprised of an HL domain, which binds specifically with a designated antigen. A dAb does not contain a VL domain, but may contain other antigen binding domains known to exist to antibodies, for example, the kappa and lambda domains. Methods for preparing dabs are known in the art. See, for example, Ward et al, Nature 341: 544 (1989).

Antibodies can also be comprised of VH and VL domains, as well as other known antigen binding domains. Examples of these types of antibodies and methods for their preparation and known in the art (see, e.g., U.S. Pat. No. 4,816,467, which is incorporated herein by reference), and include the following. For example, "vertebrate antibodies" refers to antibodies that are tetramers or aggregates thereof, comprising light and heavy chains which are usually aggregated in a "Y" configuration and which may or may not have covalent linkages between the chains. In vertebrate antibodies, the amino acid sequences of the chains are homologous with those sequences found in antibodies produced in vertebrates, whether in situ or in vitro (for example, in hybridomas). Vertebrate antibodies include, for example, purified polyclonal antibodies and monoclonal antibodies, methods for the preparation of which are described infra.

"Hybrid antibodies" are antibodies where chains are separately homologous with reference to mammalian antibody chains and represent novel assemblies of them, so that two different antigens are precipitable by the tetramer or aggregate. In hybrid antibodies, one pair of heavy and light chains are homologous to those found in an antibody raised against a first antigen, while a second pair of chains are homologous to those found in an antibody raised against a second antibody. This results in the property of "divalence", i.e., the ability to bind two antigens simultaneously. Such hybrids can also be formed using chimeric chains, as set forth below.

"Chimeric antibodies" refers to antibodies in which the heavy and/or light chains are fusion proteins. Typically, one portion of the amino acid sequences of the chain is homologous to corresponding sequences in an antibody derived from a particular species or a particular class, while the remaining segment of the chain is homologous to the sequences derived from another species and/or class. Usually, the variable region of both light and heavy chains mimics the variable regions or antibodies derived from one species of vertebrates, while the constant portions are homologous to the sequences in the antibodies derived from another species of vertebrates. However, the definition is not limited to this particular example. Also included is any antibody in which either or both of the heavy or light chains are composed of combinations of sequences mimicking the sequences in antibodies of different sources, whether these sources be from differing classes or different species of origin, and whether or not the fusion point is at the variable/constant boundary. Thus, it is possible to produce antibodies in which neither the constant nor the variable region mimic know antibody sequences. It then becomes possible, for example, to construct antibodies whose variable region has a higher specific affinity for a particular antigen, or whose constant region can elicit enhanced complement fixation, or to make other improvements in properties possessed by a particular constant region.

Another example is "altered antibodies", which refers to antibodies in which the naturally occurring amino acid sequence in a vertebrate antibody has been varies. Utilizing recombinant DNA techniques, antibodies can be redesigned to obtain desired characteristics. The possible variations are many, and range from the changing of one or more amino acids to the complete redesign of a region, for example, the constant region. Changes in the constant region, in general, to attain desired cellular process characteristics, e.g., changes in complement fixation, interaction with membranes, and other effector functions. Changes in the variable region can be made to alter antigen binding characteristics. The antibody can also be engineered to aid the specific delivery of a molecule or substance to a specific cell or tissue site. The desired alterations can be made by known techniques in molecular biology, e.g., recombinant techniques, site-directed mutagenesis, etc.

Yet another example are "univalent antibodies", which are aggregates comprised of a heavy-chain/light-chain dimer bound to the Fc (i.e., stem) region of a second heavy chain. This type of antibody escapes antigenic modulation. See, e.g., Glennie et al. Nature 295: 712 (1982). Included also within the definition of antibodies are "Fab" fragments of antibodies. The "Fab" region refers to those portions of the heavy and light chains which are roughly equivalent, or analogous, to the sequences which comprise the branch portion of the heavy and light chains, and which have been shown to exhibit immunological binding to a specified antigen, but which lack the effector Fc portion. "Fab" includes aggregates of one heavy and one light chain (commonly known as Fab'), as well as tetramers containing the 2H and 2L chains (referred to as F(ab)2), which are capable of selectively reacting with a designated antigen or antigen family. Fab antibodies can be divided into subsets analogous to those described above, i.e., "vertebrate Fab", "hybrid Fab", "chimeric Fab", and "altered Fab". Methods of producing Fab fragments of antibodies are known within the art and include, for example, proteolysis, and synthesis by recombinant techniques.

"Antigen-antibody complex" refers to the complex formed by an antibody that is specifically bound to an epitope on an antigen.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An implementation of this algorithm for nucleic acid and peptide sequences is provided by the Accelrys in their BestFit utility application. The default parameters for this method are described in the supplier's (Accelrys) materials. Other equally suitable programs for calculating the percent identity or similarity between sequences are generally known in the art.

For example, percent identity of a particular nucleotide sequence to a reference sequence can be determined using the homology algorithm of Smith and Waterman with a default scoring table and a gap penalty of six nucleotide positions. Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, such as the alignment program BLAST, which can also be used with default parameters. For example, BLASTN and BLASTP can be used with the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST.

One of skill in the art can readily determine the proper search parameters to use for a given sequence in the above programs. For example, the search parameters may vary based on the size of the sequence in question. Thus, for example, a representative embodiment of the present invention would include an isolated polynucleotide or polypeptide having X contiguous nucleotides or amino acids, wherein (i) the X contiguous nucleotides or amino acids have at least about 50% identity to Y contiguous nucleotides or amino acids derived from any of the sequences described herein, (ii) X equals Y, and (iii) X is greater than or equal to 6 nucleotides and up to 5000 nucleotides or 3 amino acids to 500 amino acids, preferably greater than or equal to 8 nucleotides and up to 5000 nucleotides or 15 amino acids to 500 amino acids, more preferably 10-12 nucleotides and up to 5000 nucleotides or 20 amino acids to 500 amino acids, including all integer values falling within the above-described ranges.

Computer programs are also available to determine the likelihood of certain polypeptides to form structures such as β-sheets. One such program, described herein, is the "ALB" program for protein and polypeptide secondary structure calculation and predication. In addition, secondary protein structure can be predicted from the primary amino acid sequence, for example using protein crystal structure and aligning the protein sequence related to the crystal structure (e.g., using Molecular Operating Environment (MOE) programs available from the Chemical Computing Group Inc., Montreal, P.Q., Canada). Other methods of predicting secondary structures are described, for example, in Garnier et al. (1996) *Methods Enzymol.* 266:540-553; Geourjon et al. (1995) *Comput. Applic. Biosci.* 11:681-684; Levin (1997) *Protein Eng.* 10:771-776; and Rost et al. (1993) *J. Molec. Biol.* 232:584-599.

Homology can also be determined by hybridization of polynucleotides under conditions that form stable duplexes between homologous regions, followed by digestion with single-stranded-specific nuclease(s), and size determination of the digested fragments. Two DNA, or two polypeptide sequences are "substantially homologous" to each other when the sequences exhibit at least about 80%-85%, preferably at least about 90%, and most preferably at least about 95%-98% sequence identity over a defined length of the molecules, as determined using the methods above. As used herein, substantially homologous also refers to sequences showing complete identity to the specified DNA or polypeptide sequence. DNA sequences that are substantially homologous can be identified in a Southern hybridization experiment under, for example, stringent conditions, as defined for that particular system. Defining appropriate: hybridization conditions is within the skill of the art. See, e.g., Sambrook et al., supra; *DNA Cloning*, supra; *Nucleic Acid Hybridization*, supra.

A "coding sequence" or a sequence that "encodes" a selected protein, is a nucleic acid sequence that is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to cDNA from viral nucleotide sequences as well as synthetic and semisynthetic DNA sequences and sequences including base analogs. A transcription termination sequence may be located 3' to the coding sequence.

"Control elements" refers collectively to promoter sequences, ribosome binding sites, polyadenylation signals, transcription termination sequences, upstream regulatory domains, enhancers, and the like, which collectively provide for the transcription and translation of a coding sequence in a host cell. Not all of these control elements need always be present so long as the desired gene is capable of being transcribed and translated.

A control element "directs the transcription" of a coding sequence in a cell when RNA polymerase will bind the promoter sequence and transcribe the coding sequence into mRNA, which is then translated into the polypeptide encoded by the coding sequence.

"Operably linked" refers to an arrangement of elements wherein the components so described are configured so as to perform their usual function. Thus, control elements operably linked to a coding sequence are capable of effecting the expression of the coding sequence when RNA polymerase is present. The control elements need not be contiguous with the coding sequence, so long as they function to direct the expression thereof. Thus, for example, intervening untranslated yet transcribed sequences can be present between, e.g., a promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

By "vertebrate subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered.

As used herein, a "biological sample" refers to a sample of tissue or fluid isolated from an individual, including but not limited to, for example, blood, plasma, serum, fecal matter, urine, bone marrow, bile, spinal fluid, lymph fluid, samples of the skin, external secretions of the skin, respiratory, intestinal, and genitourinary tracts, samples derived from the gastric epithelium and gastric mucosa, tears, saliva, milk, blood cells, organs, biopsies and also samples of in vitro cell culture constituents including but not limited to conditioned media resulting from the growth of cells and tissues in culture medium, e.g., recombinant cells, and cell components.

The terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof that is capable of exhibiting fluorescence in the detectable range. Particular examples of labels that may be used with the invention include, but are not limited to fluorescein, rhodamine, dansyl, umbelliferone, Texas red, luminol, acradimum esters, NADPH, beta-galactosidase, horseradish peroxidase, glucose oxidase, alkaline phosphatase and urease.

Overview

The present invention concerns hybrid Env-CD4 polypeptide and Env-CD4 complexes (and polynucleotides encoding the hybrids and/or complexes) as well as the use of these molecules. Without being bound by a particular theory, it appears that it has been difficult to generate immunological responses against Env because the CD4 binding site (and/or the CCR binding site) is buried between the outer domain, the inner domain and the V1/V2 domains of Env. Thus, although deletion of the V1/V2 domain may render the virus more susceptible to neutralization by monoclonal antibody directed to the CD4 site, the conformation of Env prior to CD4 binding may prevent an antibody response. Thus, the present invention provides Env polypeptides complexed to CD4 proteins (e.g., soluble or CD mini-proteins) or hybrid Env-CD4 polypeptides. Binding of CD4 to Env in these molecules causes a conformational change in Env that exposes one or more epitopes (e.g., cryptic epitopes) in or near the CD4 binding site, which in turn allows the generation of an immune response (e.g., a neutralizing antibody response) to Env.

Various forms of the different embodiments of the invention, described herein, may be combined.

Env Polypeptides

The Env polypeptide portion of the complexes described herein can be derived from an envelope protein, preferably from HIV Env. As noted above, the envelope protein of HIV-1 is a glycoprotein of about 160 kd (gp160). During virus infection of the host cell, gp160 is cleaved by host cell proteases to form gp120 and the integral membrane protein, gp41. The gp41 portion is anchored in (and spans) the membrane bilayer of virion, while the gp120 segment protrudes into the surrounding environment. As there is no covalent attachment between gp120 and gp41, free gp120 is released from the surface of virions and infected cells. Env polypeptides may also include gp140 polypeptides.

In certain embodiments, the Env polypeptide component of the complex is a monomer or a dimer. In preferred embodiments, the Env polypeptide component is an oligomeric Env polypeptide. The primary sequence of the Env polypeptide precursor of HIV-$1_{SF2}$ (hereinafter "SF2") strain is shown in FIG. 1. The gp120 amino acid sequence (including leader sequence) extends from amino acids 1-509 of FIG. 1). The polypeptide contains approximately 24 N-linked glycosylation sites that are common to most, if not all, gp120 sequences. As suggested by their name, the hypervariable domains contain extensive amino acid substitutions, insertions and deletions as between strains. (See, also, FIG. 7). Despite this variation, most, if not all, Env polypeptide sequences preserve the virus's ability to bind to the viral receptor CD4. Further, alignment of the amino acid sequences of Env polypeptide of any HIV variant can be determined relative to other variants, such as HXB-2, as described for example, in WO 00/39303. In other embodiments, the Env polypeptide comprises an oligomeric form of Env, for example oligomeric gp140 (o-gp140).

The Env polypeptide component of the Env-CD4 complex can be derived any known HIV isolates, as well as newly identified isolates, and subtypes of these isolates. Descriptions of structural features can be given herein with reference to SF2 or HXB-2. One of ordinary skill in the art in view of the teachings of the present disclosure and the art can determine corresponding regions in other HIV variants (e.g., isolates $HIV_{IIIb}$, HIV-$1_{SF162}$, HIV-$1_{SF170}$, $HIV_{LAV}$, $HIV_{LAI}$, $HIV_{MN}$, HIV-$1_{CM235}$, HIV-$1_{US4}$, other HIV-1 strains from diverse subtypes (e.g., subtypes, A through G, and O), HIV-2 strains and diverse subtypes (e.g., HIV-$2_{UC1}$ and HIV-$2_{UC2}$), and simian immunodeficiency virus (SIV). (See, e.g., Virology, 3rd Edition (W. K. Joklik ed. 1988); *Fundamental Virology*, 2nd Edition (B. N. Fields and D. M. Knipe, eds. 1991); *Virology*, 3rd Edition (Fields, B N, D M Knipe, P M Howley, Editors, 1996, Lippincott-Raven, Philadelphia, Pa.; for a description of these and other related viruses), using for example, sequence comparison programs (e.g., BLAST and others described herein) or identification and alignment of structural features (e.g., a program such as the "ALB" program described herein that can identify β-sheet regions). The actual amino acid sequences of the modified Env polypeptides can be based on any HIV variant.

The Env polypeptides described herein may include additional modifications to the native sequence, such as additional internal deletions, additions and substitutions. These modifications may be deliberate, as through site-directed mutagenesis, or may be accidental, such as through naturally occurring mutational events. Thus, for example, if the Env polypeptide is to be used in vaccine compositions, the modifications must be such that immunological activity (i.e., the ability to elicit an antibody response to the polypeptide) is not lost. Similarly, if the polypeptides are to be used for diagnostic purposes, such capability must be retained. The Env polypeptides described herein can be monomeric or oligomeric.

CD4 Mini-Proteins

In the practice of the present invention, Env polypeptides are complexed to CD proteins in order to change conformation of the Env polypeptide and expose epitopes that elicit neutralizing antibodies.

The amino acid sequence of CD4 is known and structural studies on CD4 have shown that this molecule is composed of four extracellular immunoglobulin like domains (three containing disulfide linked loops). It is also known that the binding of gp120 to its receptor (CD4) induces conformational changes in the Env protein. However only domain 1 (D1) of CD4 is critical for its interaction with gp120 (Arthos et al. (1989) *Cell* 57(3):469-81; Truneh et al. (1991) *J Biol Chem* 266(9):5942-8). Mutational analyses, antibody competition experiments combined with the knowledge of three-dimensional structure of CD4 have shown that a region homologous to complementarity determining region 2 (CDR2) of immunoglobulin in D1 plays a major role in gp120 binding (Ryu et al. (1994) *Structure* 2(1):59-74, Sullivan et al. (1998) *J Virol* 72(8):6332-8). Indeed, structure resolution of gp120:CD4 complex confirmed that the CDR2-like loop of CD4 is central in CD4-gp120 interaction (Choe & Sodroski (1992) *J Acquir Immune Defic Syndr* 5(2):204-10, Gizachew et al. (1998) *Biochemistry* 37(30):10616-25). In the complex CD4 Phe-43 side chain plugs the entrance of a deep cavity in gp120 and CD4 Arg59, just behind Phe43, is involved in a double H-bond with Asp-368 in gp120.

Crystallographic structure analysis of gp120, in complex with CD4 and the Fab portion the neutralizing monoclonal antibody 17b (Kwong et al. (1998) *Nature* 393:648-659), indicates that a large surface (742 Å2) of the domain D1 of CD4 binds to a large depression (800 Å2) on gp120. The CD4 interface is comprised by 22 residues, contributing to gp120 binding with mixed hydrophobic, electrostatic, H-bonding interactions. The large size and complexity of this interface makes the reproduction of such functional epitope into a small molecule a challenge, and explains the difficulty in the development of small molecule inhibitors of gp120-CD4 interaction. Vita et al. (1998) *Biopolymers* 47:93-100. However, in spite of the large number of residues present in gp120-CD4 interaction surface, studies on hormone-receptor systems showed that only a few residues might dominate the binding energy at the protein-protein interface. Clackson and Wells (1995) *Science* 267(5196):383-386.

Upon binding of gp120 to CD4, unique neutralizing epitopes also appear to be exposed, for example the epitope recognized by the monoclonal antibody CG10 (Gershoni et al. (1993) *Faseb J* 7(12):1185-7). Indeed, while monomeric gp120 protein from lab strains is poorly immunogenic with regard to eliciting primary isolate neutralizing antibodies (Mascola et al. (1996) *J. Infect. Dis.* 173:340-348), monoclonal antibodies that appear to recognize certain epitopes that are exposed on the Env surface once it binds to its CD4 receptor have been shown to neutralize diverse primary isolates. See, e.g., the antibody designated 17b (Thali et al. (1993) J Virol 67(7):3978-88). However, cross-clade primary isolate neutralizing antibody responses using receptor/co-receptor complexed Env have been attributed to the immunogenicity of the gp41 fusion domain. Lacasse et al (1999) *Science* 283:357-362.

Additionally, attempts to evaluate gp120-CD4 complexes as potential vaccine candidate for inducing high avidity and primary isolate neutralizing antibodies have been thwarted by the concern that an immune response could be generated against CD4 itself thereby raising autoimmune and safety issues. (D'Souza et al. (1997) *J Infect Dis.* 175:1056-62, DeVico et al. (1995) *Virology* 211(2):583-8). Since the structure of CD4 was solved, attempts were made by several groups to identify minimum gp120 binding domain of CD4 that can retain gp120 binding activity (118).

Thus, the present invention makes use of less than full-length CD4 proteins or CD4 mimics complexed to an Env protein. Preferably, the CD miniproteins complexed to Env comprises sequences are derived from or functionally mimic the D1 domain of CD4. In preferred embodiments, the CD4 mini-protein is derived from, and/or exhibits structural similarity to, the CDR2-like loop of CD4. Non-limiting examples of CD4 mini proteins includes SEQ ID NO:1-4 (Example 4). Structural similarity can be determined as described herein.

(Vita et al. (1999) *Proc Natl Acad Sci USA* 96(23):13091-6 and Martin et al. (2003) *Nat. Biotech.* 21:71-76) describe an additional non-limiting example of a polypeptide having sequence and/or structural homology to CDR2-like loop of CD4 is the scorpion toxin scyllatoxin (31 residues only) that contains a solvent exposed β-hairpin. When its backbone atoms are superimposed on the CDR2-like loop of CD4, (sequence 36-47), an RMS deviation of only 1.1 Å is found.

One of skill in the art can readily determine amino acid sequences that exhibit structural and/or amino acid similarity to the D1 domain of CD4 in view of the teachings herein. Further, any of these homologs (structural or sequence), can be further modified. Such modifications can affect structure and/or function. For example, amino acid substitutions, additions and/or deletions can be made to the mini-proteins such that the gp120 binding structure is preserved or enhanced.

Additional modifications, for example to destroy unwanted functions, can also be made. For example, as described in Vita et al. (1999) *Proc Natl Acad Sci USA* 96(23):13091-6 and Martin et al. (2003) *Nat. Biotech.* 21:71-76, a mimetic was generated from scorpion scyllatoxin that preserved the structurally important Cys residues of the scaffold, and, additionally, included the solvent-exposed Gly38, Gln40 to Phe43, Thr45 and Gly47 of CD4 in structurally equivalent regions of the scyllatoxin β-hairpin. To further increase the structural mimicry with the CD4, an Arg and a Lys were included at positions 7 and 18, topologically equivalent to the functional Arg59 and Lys35 of CD4, respectively. To destroy the original $K^+$ channel binding function of scyllatoxin, Arg6 and Arg13 were mutated into Ala and Lys, respectively. Finally two residues both at the N- and C-terminus were deleted (Vita et al. (1999) *Proc Natl Acad Sci USA* 96(23):13091-6; Martin et al. (2003) *Nat. Biotech.* 21:71-76).

Any of the CD4 mini-proteins useful in the practice of the invention can be chemically synthesized. Preferably, the synthesis is conducted under conditions that allow and promote efficient folding of the mini-protein into a conformation that binds gp120 and exposes epitopes in or near the CD4 binding site. For example, the mini-protein can be synthesized under conditions that produce a circular dichroism spectrum similar to that of scyllatoxin, in spite of mutations in the native sequence.

Hybrid Env-CD4 Proteins

In certain aspects, the Env-CD4 molecules are hybrid proteins. In one embodiment, the hybrids have at least one CD4 protein (e.g., CD4 mini-protein) inserted into an Env sequence. In other embodiments, the CD4 sequence(s) precede or follow the Env polypeptide (e.g., by at the N or C terminal of the Env polypeptide). Further, any of the hybrids may include one or more linkers of varying length (e.g., 3-30 amino acids in length, or any integer therebetween). In certain embodiments, the Env-CD4 hybrids are fusion proteins encoded by one or more polynucleotide sequences.

Suitable CD4 sequences for use Env-CD4 hybrids are described above. As noted above, CD4 miniproteins complexed to Env comprises sequences are preferably derived from or functionally mimic the D1 domain of CD4. In preferred embodiments, the CD4 mini-protein is derived from, and/or exhibits structural similarity to, the CDR2-like loop of CD4. Non-limiting examples of CD4 mini proteins includes SEQ ID NO:1-4 (Example 4) or CD4 mimetics (such as those described in Vita et al. (1999) *Proc Natl Acad Sci USA* 96(23): 13091-6 and Martin et al. (2003) *Nat. Biotech.* 21:71-76).

The CD4 mini-protein can be of any length, for example between about 10 and about 200 amino acids in length (or any integer therebetween), preferably between about 20 and about 100 amino acids in length, and more preferably between about 25 and about 85 amino acids in length (or any integer value therebetween). One of skill in the art can readily determine amino acid sequences that exhibit structural and/or amino acid similarity to the D1 domain of CD4 (and/or SEQ ID NO:1-4) in view of the teachings herein. Further, any of these homologs (structural or sequence), can be further modified.

Typically, the CD4 polypeptide is inserted into any Env polypeptide described herein, for example, gp120, gp140, o-gp140, gp160 or fragments thereof. In addition, the Env sequence can contain modifications, for example, deletions, truncations and/or substitutions. In certain embodiments, one or more of the variable regions (V1 though V5) are deleted and/or truncated. For example, the CD4 sequence can be inserted into one of these variable regions. It is preferable, although not required, that the CD4 sequence be a single, contiguous sequence. In certain embodiments, the deleted variable regions are replaced with a shorter polypeptide sequences (e.g., 3-20 amino acid sequence or any integer therebetween), as these shorter polypeptides may maintain of the overall conformation of the Env protein and/or provide the flexibility needed to allow for binding of the CD4 protein to Env (Example 4).

As will be readily apparently, one or more elements of the Env-CD4 hybrids may contain further modifications. Such modifications can affect structure and/or function. For example, amino acid substitutions, additions and/or deletions can be made to the mini-proteins such that the gp120 binding structure is preserved or enhanced.

Any of the hybrid Env-CD4 proteins useful in the practice of the invention can be chemically synthesized. Preferably, the synthesis is conducted under conditions that allow and promote efficient folding of the mini-protein into a conformation that binds gp120 and exposes epitopes in or near the CD4 binding site. Further, as described in detail below, hybrid Env-CD4 proteins can be produced recombinantly.

Polypeptide Production

The CD4 mini-proteins, Env polypeptides and hybrid Env-CD4 polypeptides of the present invention can be produced in any number of ways all of which are well known in the art.

In one embodiment, the polypeptides are generated using recombinant techniques, well known in the art. In this regard, oligonucleotide probes can be devised based on the known sequences of the Env (e.g., gp120) polypeptide genome and used to probe genomic or cDNA libraries for Env genes. The gene can then be further isolated using standard techniques and, e.g., restriction enzymes employed to truncate the gene at desired portions of the full-length sequence. Similarly, the Env gene(s) can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The genes encoding the modified or hybrid (e.g., truncated and/or substituted) Env and/or CD4 polypeptides can be produced synthetically, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223: 1299; Jay et al. (1984) *J. Biol. Chem.* 259:6311; Stemmer et al. (1995) *Gene* 164:49-53.

Recombinant techniques are readily used to clone a gene encoding an Env polypeptide gene that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci. USA* (1982) 79:6409.

Once coding sequences for the desired Env and/or CD4 proteins have been isolated or synthesized, they can be cloned into any suitable vector or replicon for expression. As will be apparent from the teachings herein, a wide variety of vectors encoding modified polypeptides can be generated by creating expression constructs which operably link, in various combinations, polynucleotides encoding Env and/or CD4 polypeptides having deletions or mutation therein. Thus, polynucleotides encoding a particular Env having modified (e.g., deleted and/or substituted) variable regions (e.g., V1/V2) can be operably linked with polynucleotides encoding polypeptides having deletions or replacements in the small loop region and the construct introduced into a host cell for polypeptide expression. Non-limiting examples of such combinations are discussed in the Examples.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-K coli gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the modified Env proteins. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides or heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding to sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; DNA Cloning, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as *E. coli, Bacillus subtilis*, and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda*, and *Trichoplusia ni.*

Depending on the expression system and host selected, the proteins of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, an interferon ($\gamma$ or $\alpha$) signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the Env polypeptides substantially intact. Intracellular proteins can also be obtained by removing components from the cell wall or membrane, e.g., by the use of detergents or organic solvents, such that leakage of the Env polypeptides occurs. Such methods are known to those of skill in the art and are described in, e.g., *Protein Purification Applications: A Practical Approach*, (E. L. V. Harris and S. Angal, Eds., 1990).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced Env polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular Env polypeptides of the present invention involves affinity purification, such as by immunoaffinity chromatography using anti-Env specific antibodies, or by lectin affinity chromatography. Particularly preferred lectin resins are those that recognize mannose moieties such as but not limited to resins derived from *Galanthus nivalis* agglutinin (GNA), *Lens culinaris* agglutinin (LCA or lentil lectin), *Pisum sativum* agglutinin (PSA or pea lectin), *Narcissus pseudonarcissus* agglutinin (NPA) and *Allium ursinum* agglutinin (AUA). The choice of a suitable affinity resin is within the skill in the art. After affinity purification, the polypeptides can be further purified using conventional techniques well known in the art, such as by any of the techniques described above.

Relatively small polypeptides, i.e., up to about 50-100 amino acids in length, can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, *Solid Phase Peptide Synthesis* (Pierce Chemical Co., Rockford, Ill. 1984) and G. Barany and R. B. Merrifield, *The Peptides Analysis, Synthesis, Biology*, editors E. Gross and J. Meienhofer, Vol. 2, (Academic Press, New York, 1980), pp. 3-254, for solid phase peptide synthesis techniques; and M. Bodansky, *Principles of Peptide Synthesis*, (Springer-Verlag, Berlin 1984) and E. Gross and J. Meienhofer, Eds., *The Peptides: Analysis, Synthesis, Biology*, Vol. 1, for classical solution synthesis.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

The polypeptide analogs of the present invention can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

Env-CD4 Complexes

Env and CD4 proteins can be produced as hybrids (e.g., fusion) proteins as described herein. In addition, Env and CD4 proteins can be separately produced and complexed to each other in a variety of ways. In certain embodiments, Env and CD4 proteins are complexed using one or more crosslinking agents, such as formaldehyde, glutyraldehyde and the like. An alternative strategy will be to link CD4 miniprotein to the envelope by a specific covalent bond which will not perturb the envelope exposed antigenic surface, yet it will expose the cryptic conserved epitopes that are normally not accessible, for example so that an antibody response can be mounted. In still further embodiments, a fixative such as formalin is used to complex Env and CD4 proteins.

In addition, suitable complexes may be produced by e.g., co-transfecting host cells with constructs encoding hybrid Env-CD4 proteins, Env (e.g., gp120), CD4 mini-proteins and/or other polypeptides of the desired complex. Co-transfection can be accomplished either in trans or cis, i.e., by using separate vectors or by using a single vector that bears both of the Env and the CD4 mini-protein(s). If done using a single vector, both genes can be driven by a single set of control elements. A single set of control elements is preferably employed in the case of constructs encoding Env-CD4 hybrid proteins (see, e.g., Example 4). Alternatively, the Env- and CD4 mini protein-encoding genes can be present on the vector in individual expression cassettes, driven by individual control elements. Following expression, the proteins may spontaneously associate. Alternatively, the complexes can be formed by mixing the individual proteins together which have been produced separately, either in purified or semi-purified form, or even by mixing culture media in which host cells expressing the proteins, have been cultured. See, International Publication No. WO 96/04301, published Feb. 15, 1996, for a description of such complexes.

Antibodies

Antibodies, both monoclonal and polyclonal, which are directed against Env-CD4 mini protein complexes epitopes (and cryptic epitopes exposed by binding of CD4 to Env) are particularly useful in diagnosis and therapeutic applications, for example, those antibodies which are neutralizing are useful in passive immunotherapy. Monoclonal antibodies, in particular, may be used to raise anti-idiotype antibodies.

Anti-idiotype antibodies are immunoglobulins that carry an "internal image" of the antigen of the infectious agent against which protection is desired. Techniques for raising anti-idiotype antibodies are known in the art. See, e.g., Grzych (1985), Nature 316:74; MacNamara et al. (1984), Science 226:1325, Uytdehaag et al (1985), J. Immunol. 134: 1225. These anti-idiotype antibodies may also be useful for treatment and/or diagnosis of HIV.

An immunoassay for viral antigen may use, for example, a monoclonal antibody directed towards a viral epitope, a combination of monoclonal antibodies directed towards epitopes of one viral polypeptide, monoclonal antibodies directed towards epitopes of different viral polypeptides, polyclonal antibodies directed towards the same viral antigen, polyclonal antibodies directed towards different viral antigens or a combination of monoclonal and polyclonal antibodies.

Immunoassay protocols may be based, for example, upon competition, or direct reaction, or sandwich type assays. Protocols may also, for example, use solid supports, or may be by immunoprecipitation. Most assays involve the use of labeled antibody or polypeptide. The labels may be, for example, fluorescent, chemiluminescent, radioactive, or dye molecules. Assays that amplify the signals from the probe are also known. Examples of which are assays that utilize biotin and avidin, and enzyme-labeled and mediated immunoassays, such as ELISA assays.

An enzyme-linked immunosorbent assay (ELISA) can be used to measure either antigen or antibody concentrations. This method depends upon conjugation of an enzyme to either an antigen or an antibody, and uses the bound enzyme activity as a quantitative label. To measure antibody, the known antigen is fixed to a solid phase (e.g., a microplate or plastic cup), incubated with test serum dilutions, washed, incubated with anti-immunoglobulin labeled with an enzyme, and washed again. Enzymes suitable for labeling are known in the art, and include, for example, horseradish peroxidase. Enzyme activity bound to the solid phase is measured by adding the specific substrate, and determining product formation or substrate utilization colorimetrically. The enzyme activity bound is a direct function of the amount of antibody bound.

To measure antigen, a known specific antibody is fixed to the solid phase, the test material containing antigen is added, after an incubation the solid phase is washed, and a second enzyme-labeled antibody is added. After washing, substrate is added, and enzyme activity is estimated colorimetrically, and related to antigen concentration.

Polyclonal antibodies can be produced by administering the fusion protein to a mammal, such as a mouse, a rabbit, a goat, or a horse. Serum from the immunized animal is collected and the antibodies are purified from the plasma by, for example, precipitation with ammonium sulfate, followed by chromatography, preferably affinity, chromatography. Techniques for producing and processing polyclonal antisera are known in the art.

Monoclonal antibodies directed against epitopes exposed by binding of CD4 to Env (e.g., cryptic epitopes) can also be produced. Normal B cells from a mammal, such as a mouse, immunized with, e.g., an Env-CD4 complex as described herein can be fused with, for example, HAT-sensitive mouse myeloma cells to produce hybridomas. Hybridomas producing antibodies specific for epitopes exposed when CD4 mini-proteins bind to Env can be identified using RIA or ELISA and isolated by cloning in semi-solid agar or by limiting dilution. Clones producing the desired specific antibodies are isolated by another round of screening.

Antibodies, either monoclonal and polyclonal, which are directed against epitopes, are particularly useful for detecting the presence of antigens in a sample, such as a serum sample from an HIV-infected human. An immunoassay for an HIV antigen may utilize one antibody or several antibodies. An immunoassay for an HIV antigen may use, for example, a monoclonal antibody directed towards an HIV epitope, a combination of monoclonal antibodies directed towards epitopes of one Env or Env-CD4 polypeptide, monoclonal antibodies directed towards epitopes of different polypeptides, polyclonal antibodies directed towards the same HIV antigen, polyclonal antibodies directed towards different HIV antigens, or a combination of monoclonal and polyclonal antibodies. Immunoassay protocols may be based, for example, upon competition, direct reaction, or sandwich type assays using, for example, labeled antibody. The labels may be, for example, fluorescent, chemiluminescent, or radioactive.

The polyclonal or monoclonal antibodies may further be used to isolate Env or CD4 complexed-Env by immunoaffinity columns. The antibodies can be affixed to a solid support by, for example, adsorption or by covalent linkage so that the antibodies retain their immunoselective activity. Optionally, spacer groups may be included so that the antigen binding site of the antibody remains accessible. The immobilized antibodies can then be used to bind the target from a biological sample, such as blood or plasma. The bound proteins or complexes are recovered from the column matrix by, for example, a change in pH.

In still further aspects, any of the antibodies generated as described herein (e.g., monoclonal antibodies) can be used to identify epitopes in Env that may be involved in virus neutralization (e.g., cryptic) epitopes. For example, an epitope recognized by an antibody generated as described herein can be identified and then used to generate further antibodies (e.g., neutralizing antibodies). Methods of identifying epitopes recognized by antibodies are known to those of skill in the art.

Diagnostic, Vaccine and Therapeutic Applications

The Env-CD4 hybrids and/or complexes of the present invention (or the polynucleotides coding therefor), can be used for a number of diagnostic and therapeutic purposes. For example, the proteins and polynucleotides or antibodies generated against the same, can be used in a variety of assays, to determine the presence of reactive antibodies/and or Env proteins in a biological sample to aid in the diagnosis of HIV infection or disease status or as measure of response to immunization.

As noted above, the presence of antibodies reactive with the Env (e.g., gp120) polypeptides and, conversely, antigens reactive with antibodies generated thereto, can be detected using standard electrophoretic and immunodiagnostic techniques, including immunoassays such as competition, direct reaction, or sandwich type assays. Such assays include, but are not limited to, western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, or enzymatic labels or dye molecules, or other methods for detecting the formation of a complex between the antigen and the antibody or antibodies reacted therewith.

Solid supports can be used in the assays such as nitrocellulose, in membrane or microtiter well form; polyvinylchloride, in sheets or microtiter wells; polystyrene latex, in beads or microtiter plates; polyvinylidine fluoride; diazotized paper; nylon membranes; activated beads, and the like.

Typically, the solid support is first reacted with the biological sample (or the gp120 proteins), washed and then the antibodies, (or a sample suspected of containing antibodies), applied. After washing to remove any non-bound ligand, a secondary binder moiety is added under suitable binding conditions, such that the secondary binder is capable of associating selectively with the bound ligand. The presence of the secondary binder can then be detected using techniques well known in the art. Typically, the secondary binder will comprise an antibody directed against the antibody ligands. A number of anti-human immunoglobulin (Ig) molecules are known in the art (e.g., commercially available goat anti-human Ig or rabbit anti-human Ig). Ig molecules for use herein will preferably be of the IgG or IgA type, however, IgM may also be appropriate in some instances. The Ig molecules can be readily conjugated to a detectable enzyme label, such as horseradish peroxidase, glucose oxidase, Beta-galactosidase, alkaline phosphatase and urease, among others, using methods known to those of skill in the art. An appropriate enzyme substrate is then used to generate a detectable signal.

Alternatively, a "two antibody sandwich" assay can be used to detect the proteins of the present invention. In this technique, the solid support is reacted first with one or more of the antibodies directed against Env (e.g., gp120), washed and then exposed to the test sample. Antibodies are again added and the reaction visualized using either a direct color reaction or using a labeled second antibody, such as an anti-immunoglobulin labeled with horseradish peroxidase, alkaline phosphatase or urease.

Assays can also be conducted in solution, such that the viral proteins and antibodies thereto form complexes under precipitating conditions. The precipitated complexes can then be separated from the test sample, for example, by centrifugation. The reaction mixture can be analyzed to determine the presence or absence of antibody-antigen complexes using any of a number of standard methods, such as those immunodiagnostic methods described above.

The Env-CD4 molecules, produced as described above, or antibodies to the complexes, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

The Env-CD4 complexes and/or hybrids (and polynucleotides encoding the component polypeptides) can also be used in vaccine compositions, individually or in combination, in e.g., prophylactic (i.e., to prevent infection) or therapeutic (to treat HIV following infection) vaccines. The vaccines can comprise mixtures of one or more of the complexes and/or hybrids (or nucleotide sequences encoding these molecules), such as Env (e.g., gp120) proteins derived from more than one viral isolate. The vaccine may also be administered in conjunction with other antigens and immunoregulatory agents, for example, immunoglobulins, cytokines, lymphokines, and chemokines, including but not limited to IL-2, modified IL-2 (cys125-ser125), GM-CSF, IL-12, alpha- or gamma-interferon, IP-10, MIP1 and RANTES. The vaccines may be administered as polypeptides or, alternatively, as naked nucleic acid vaccines (e.g., DNA), using viral vectors (e.g., retroviral vectors, adenoviral vectors, adeno-associated viral vectors, alphaviral vectors) or non-viral vectors (e.g., liposomes, particles coated with nucleic acid or protein). The vaccines may also comprise a mixture of protein and nucleic acid, which in turn may be delivered using the same or different vehicles. The vaccine may be given more than once (e.g., a "prime" administration followed by one or more "boosts") to achieve the desired effects. The same composition can be administered as the prime and as the one or more boosts. Alternatively, different compositions can be used for priming and boosting.

The vaccines will generally include one or more "pharmaceutically acceptable excipients or vehicles" such as water, saline, glycerol, ethanol, etc. Additionally, auxiliary substances, such as wetting or emulsifying agents, pH buffering substances, and the like, may be present in such vehicles.

A carrier is optionally present which is a molecule that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Furthermore, the Env polypeptide may be conjugated to a bacterial toxoid, such as toxoid from diphtheria, tetanus, cholera, etc.

Adjuvants may also be used to enhance the effectiveness of the vaccines. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

Microparticles are also useful as adjuvants. These are preferably derived from a poly(α-hydroxy acid), in particular, from a poly(lactide) ("PLA"), a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials that have a variety of molecular weights and, in the case of the copolymers such as PLG, a variety of lactide:glycolide ratios, the selection of which will be largely a matter of choice, depending in part on the coadministered antigen.

The molecules (hybrids, complexes (or polynucleotides encoding the same) and/or adjuvants) may be entrapped within the microparticles, or may be adsorbed to them. Entrapment within PLG microparticles is preferred. PLG microparticles are discussed in further detail in Morris et al., (1994), Vaccine, 12:5-11, in chapter 13 of Mucosal Vaccines, eds. Kiyono et al., Academic Press 1996 (ISBN 012410587), and in chapters 16 & 18 of *Vaccine design: the subunit and adjuvant approach*, eds. Powell & Newman, Plenum Press 1995 (ISBN 0-306-44867-X).

LT mutants may advantageously be used in combination with microparticle-entrapped antigen, resulting in significantly enhanced immune responses.

Typically, the vaccine compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above.

The vaccines will comprise a therapeutically effective amount of the Env-CD4 molecules (complexes and/or hybrids) or nucleotide sequences encoding the same, antibodies directed to these molecules and any other of the above-mentioned components, as needed. By "therapeutically effective amount" is meant an amount that will induce a protective immunological response in the uninfected, infected or unexposed individual to whom it is administered. Such a response will generally result in the development in the subject of a secretory, cellular and/or antibody-mediated immune response to the vaccine. Usually, such a response includes but is not limited to one or more of the following effects; the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell.

Preferably, the effective amount is sufficient to bring about treatment or prevention of disease symptoms. The exact amount necessary will vary depending on the subject being treated; the age and general condition of the individual to be treated; the capacity of the individual's immune system to synthesize antibodies; the degree of protection desired; the severity of the condition being treated; the particular Env-CD4 complex selected and its mode of administration, among other factors. An appropriate effective amount can be readily determined by, one of skill in the art. A "therapeutically effective amount" will fall in a relatively broad range that can be determined through routine trials.

Once formulated, the nucleic acid vaccines may be accomplished with or without viral vectors, as described above, by injection using either a conventional syringe or a gene gun, such as the Accell® gene delivery system (PowderJect Technologies, Inc., Oxford, England). Delivery of DNA into cells of the epidermis is particularly preferred as this mode of administration provides access to skin-associated lymphoid cells and provides for a transient presence of DNA in the recipient. Both nucleic acids and/or peptides can be injected or otherwise administered either subcutaneously, epidermally, intradermally, intramucosally such as nasally, rectally and vaginally, intraperitoneally, intravenously, orally or intramuscularly. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

Polynucleotide Delivery

As noted above, polynucleotide sequences coding for the above-described molecules (hybrids and/or complexes) can be obtained using recombinant methods, such as by screening cDNA and genomic libraries from cells expressing the gene, or by deriving the gene from a vector known to include the same. Furthermore, the desired gene can be isolated directly from cells and tissues containing the same, using standard techniques, such as phenol extraction and PCR of cDNA or genomic DNA. See, e.g., Sambrook et al., supra, for a description of techniques used to obtain and isolate DNA. The gene of interest can also be produced synthetically, rather than cloned. The nucleotide sequence can be designed with the appropriate codons for the particular amino acid sequence desired. In general, one will select preferred codons for the intended host in which the sequence will be expressed. The complete sequence is assembled from overlapping oligonucleotides prepared by standard methods and assembled into a complete coding sequence. See, e.g., Edge, *Nature* (1981) 292:756; Nambair et al., *Science* (1984) 223:1299; Jay et al., *J. Biol. Chem.* (1984) 259:6311; Stemmer, W. P. C., (1995) *Gene* 164:49-53.

Next, the gene sequence encoding the desired can be inserted into a vector. Insertions can be made within the coding sequence or at either end of the coding sequence. Vectors may include control elements operably linked to the coding sequence, which allow to for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

The constructs may be uni-cistronic or, alternatively, multi-cistronic cassettes (e.g., bi-cistronic cassettes) can be constructed allowing expression of multiple antigens from a single mRNA using the EMCV IRES, or the like.

Once complete, the constructs are used for nucleic acid immunization using standard gene delivery protocols. Methods for gene delivery are known in the art. See, e.g., U.S. Pat. Nos. 5,399,346, 5,580,859, 5,589,466. Genes can be delivered either directly to the vertebrate subject or, alternatively, delivered ex vivo, to cells derived from the subject and the cells reimplanted in the subject.

A number of viral based systems have been developed for gene transfer into mammalian cells. For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman, *BioTechniques* (1989) 7:980-990; Miller, A. D., *Human Gene Therapy* (1990) 1:5-14; Scarpa et al., *Virology* (1991) 180:849-852; Burns et al., *Proc. Natl. Acad. Sci. USA* (1993) 90:8033-8037; and Boris-Lawrie and Temin, *Cur. Opin. Genet. Develop.* (1993) 3:102-109.

A number of adenovirus vectors have also been described. Unlike retroviruses which integrate into the host genome, adenoviruses persist extrachromosomally thus minimizing the risks associated with insertional mutagenesis (Haj-Ahmad and Graham, *J. Virol.* (1986) 57:267-274; Bett et al., *J. Virol.* (1993) 67:5911-5921; Mittereder et al., *Human Gene Therapy* (1994) 5:717-729; Seth et al., *J. Virol.* (1994) 68:933-940; Barr et al., *Gene Therapy* (1994) 1:51-58; Berkner, K. L. *BioTechniques* (1988) 6:616-629; and Rich et al., *Human Gene Therapy* (1993) 4:461-476).

Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., *Molec. Cell. Biol.* (1988) 8:3988-3996; Vincent et al., *Vaccines* 90 (1990) (Cold Spring Harbor Laboratory Press); Carter, B. J. *Current Opinion in Biotechnology* (1992) 3:533-539; Muzyczka, N. *Current Topics in Microbiol. and Immunol.* (1992) 158:97-129; Kotin, R. M. *Human Gene Therapy* (1994) 5:793-801; Shelling and Smith, *Gene Therapy* (1994) 1:165-169; and Zhou et al., *J. Exp. Med.* (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the antigens of interest include those derived from the pox family of viruses, including vaccinia virus and avian poxvirus. By way of example, vaccinia virus recombinants expressing the genes can be constructed as follows. The DNA is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected to by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., *J. Biol. Chem.* (1993) 268:6866-6869 and Wagner et al., *Proc. Natl. Acad. Sci. USA* (1992) 89:6099-6103, can also be used for gene delivery.

Members of the Alphavirus genus, such as, but not limited to, vectors derived from the Sindbis, Semliki Forest, and Venezuelan Equine Encephalitis viruses, will also find use as viral vectors for delivering the polynucleotides of the present invention. For a description of Sindbis-virus derived vectors useful for the practice of the instant methods, see, Dubensky et al., *J. Virol.* (1996) 70:508-519; and International Publication Nos. WO 95/07995 and WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference.

A vaccinia based infection/transfection system can be conveniently used to provide for inducible, transient expression of the coding sequences of interest in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, *Proc. Natl. Acad. Sci. USA* (1990) 87:6743-6747; Fuerst et al., *Proc. Natl. Acad. Sci. USA* (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase that in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, *J. Mol. Biol.* (1986) 189:113-130; Deng and Wolff, *Gene* (1994) 143:245-249; Gao et al., *Biochem. Biophys. Res. Commun.* (1994) 200:1201-1206; Gao and Huang, *Nuc. Acids Res.* (1993) 21:2867-2872; Chen et al., *Nuc. Acids Res.* (1994) 22:2114-2120; and U.S. Pat. No. 5,135,855.

Polynucleotides encoding hybrids and/or complexes as described herein can also be delivered without a viral vector. For example, the construct can be packaged in liposomes prior to delivery to the subject or to cells derived therefrom. Lipid encapsulation is generally accomplished using liposomes that are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, *Biochim. Biophys. Acta.* (1991) 1097:1-17; Straubinger et al., in *Methods of Enzymology* (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., *Proc. Natl. Acad. Sci. USA* (1987) 84:7413-7416); mRNA (Malone et al., *Proc. Natl. Acad. Sci. USA* (1989) 86:6077-6081); and purified transcription factors (Debs et al., *J. Biol. Chem.* (1990) 265:10189-10192), in functional form.

Cationic liposomes are readily available. For example, N[1-2,3-dioleyloxy)propyl]-N,N,N-triethyl-ammonium (DOTMA) liposomes are available under the trademark Lipofectin, from GIBCO BRL, Grand Island, N.Y. (See, also, Felgner et al., *Proc. Natl. Acad. Sci. USA* (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., *Proc. Natl. Acad. Sci. USA* (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., *Proc. Natl. Acad. Sci. USA* (1978) 75:4194-4198; Papahadjopoulos et al., *Biochim. Biophys. Acta* (1975) 394:483; Wilson et al., *Cell* (1979) 17:77); Deamer and Bangham, *Biochim. Biophys. Acta* (1976) 443:629; Ostro et al., *Biochem. Biophys. Res. Commun.* (1977) 76:836; Fraley et al., *Proc. Natl. Acad. Sci. USA* (1979) 76:3348); Enoch and Strittmatter, *Proc. Natl. Acad. Sci. USA* (1979) 76:145); Fraley et al., *J. Biol. Chem.* (1980) 255:10431; Szoka and Papahadjopoulos, *Proc. Natl. Acad. Sci. USA* (1978) 75:145; and Schaefer-Ridder et al., *Science* (1982) 215:166.

The DNA and/or protein(s) can also be delivered in cochleate lipid compositions similar to those described by Papahadjopoulos et al., *Biochem. Biophys. Acta.* (1975) 394:483-491. See, also, U.S. Pat. Nos. 4,663,161 and 4,871,488.

The polynucleotides of interest may also be encapsulated, adsorbed to, or associated with, particulate carriers. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; McGee J P, et al., *J Microencapsul.* 14(2):197-210, 1997; O'Hagan D T, et al., *Vaccine* 11(2):149-54, 1993. Suitable microparticles may also be manufactured in the presence of charged detergents, such as anionic or cationic detergents, to yield microparticles with a surface having a net negative or a net positive charge. For example, microparticles manufactured with anionic detergents, such as hexadecyltrimethylammonium bromide (CTAB), i.e. CTAB-PLG microparticles, adsorb negatively charged macromolecules, such as DNA. (see, e.g., Intl Application Number PCT/US99/17308).

Furthermore, other particulate systems and polymers can be used for the in vivo or ex vivo delivery of the gene of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., *Advanced Drug Delivery Reviews* (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering polynucleotides of the present invention. The particles are coated with the polynucleotide(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, *Vaccine* 12:1503-1509, 1994; Bioject, Inc., Portland, Oreg.).

Recombinant vectors carrying polynucleotides of the present invention are formulated into compositions for delivery to the vertebrate subject. These compositions may either be prophylactic (to prevent infection) or therapeutic (to treat disease after to infection). The compositions will comprise a "therapeutically effective amount" of the gene of interest such that an amount of the antigen can be produced in vivo so that an immune response is generated in the individual to which it is administered. The exact amount necessary will vary depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials.

The polynucleotide compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, pH buffering substances, and the like, may be present in such vehicles. Certain facilitators of nucleic acid uptake and/or expression can also be included in the compositions or coadministered, such as, but not limited to, bupivacaine, cardiotoxin and sucrose.

Once formulated, the compositions of the invention can be administered directly to the subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation (see, e.g., Draghia et al. (2002) *Technol Cancer Res Treat* October; 1(5):365-72; Heller (2002) *Technol Cancer Res Treat* October; 1(5):317-8), encapsulation of the polynucleotide(s) (with or without the corresponding antigen) in liposomes, and direct microinjection of the DNA into nuclei.

Direct delivery of compositions described herein in vivo will generally be accomplished with or without viral vectors, as described above, by injection using either a conventional syringe or a gene gun, such as the Accell® gene delivery system (PowderJect Technologies, Inc., Oxford, England). The constructs can be injected either subcutaneously, epidermally, intradermally, intramucosally such as nasally, rectally and vaginally, intraperitoneally, intravenously, orally or intramuscularly. Delivery of DNA into cells of the epidermis is particularly preferred as this mode of administration provides access to skin-associated lymphoid cells and provides for a transient presence of DNA in the recipient. Other modes of administration include oral and pulmonary administration, suppositories, needle-less injection, transcutaneous and transdermal applications. Dosage treatment may be a single dose schedule or a multiple dose schedule. Administration of nucleic acids may also be combined with administration of peptides or other substances.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art to which the invention pertains.

EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Preparation of gp120-Soluble CD4 (gp120-sCD4) Complexes

Figure 4:
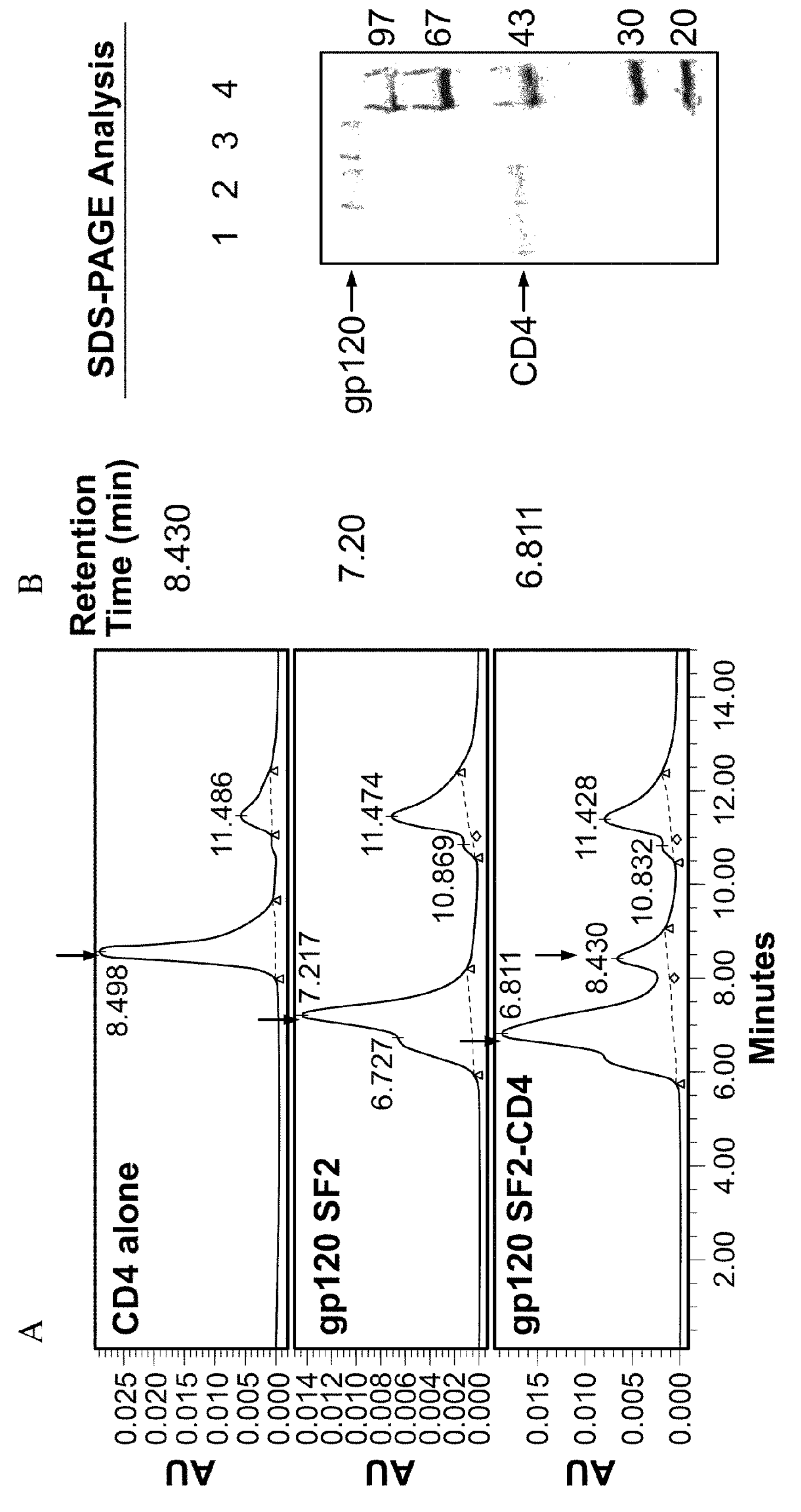
FIG. 4, panels A and B, depict characterization of gp120-CD4 complexes using size exclusion chromatography (panel A) and SDS-PAGE (panel B). The profiles and retention times of gp120, CD4 alone and as a complex as obtained using a size exclusion column (Panel A). SDS-PAGE analysis of CD4 (lane 1), gp120 SF2 (lane 3) and gp120-CD4 complex (lane 2). Molecular weight markers are shown in lane-4.

Stable purified gp120-sCD4 complexes were prepared with and without formaldehyde or formalin treatment. To induce conformational changes in the gp120, equimolar concentration of gp120 (SF2) and sCD4 were incubated together at 37° C. for one hour. At the cellular level, these interactions are transient. Therefore, at the end of incubation, half of the complexes were fixed with formaldehyde or formalin while the other half remained untreated. Both the treated and untreated complexes were separated on Superdex-200 column. Purified fractions were analyzed on an HPLC column and on SDS-PAGE (FIG. 4, panels A and B). The purified complexes contained both gp120 and CD4 together. Furthermore, these complexes appeared to be homogeneous and did not contain more than 2-3% of free sCD4.

Example 2

Rational Design of a CD4 Mini-Protein

The CD4 miniprotein, CDM3 was "rationally" designed as described in Vita et al. (1999) *Proc Natl Acad Sci USA* 96(23): 13091-6, using a structure and function relationship approach. In a first step, the three-dimensional structure of CD4 miniprotein was determined by 1H-NMR spectroscopy. This analysis showed that the miniprotein contained the α/β fold characteristic of the scorpion scaffold, and importantly, that the putative active site, transferred from CD4, was very well defined. The backbone atoms of the sequence 17-26 of CD4M3 could be superimposed on the corresponding atoms of the sequence 37-46 of native CD4 with a RMS deviation of 0.61 Å only. Furthermore, the side chains of Gln20, Ser22, Phe23 and Thr25 had an orientation very similar to that of the corresponding side chains in CD4. In particular, the Phe23 side chain was very well defined because of many long-range contacts observed. This side chain protruded into the solvent in a conformation that is rather unusual for a hydrophobic moiety, but is reminiscent of that of Phe43 of CD4, which, in the crystal structure of the CD4-gp120 complex, is seen to plug the entrance of the "Phe43 cavity" of gp120 (Kwong et al. (1998) *Nature* 393:648-659). Lys16, Arg7 side chains and Gly27, however, diverged from the structure of the corresponding Lys35, Arg59 and strand C" of CD4.

In a second step, each putatively active side chain of the miniprotein was replaced by an Ala residue ("Ala scanning"). The effect of alanine substitution on gp120 binding, determined by competitive ELISA, clearly indicated that each transferred residue played a different functional role, and pointed to a Phe residue present at the apex of the β-hairpin, as a "hot spot" of the chimera active surface. This is in agreement with the data obtained on mutagenesis of recombinant CD4 (Arthos et al. (1989) *Cell* 57(3):469-81; Binley et al. (1997) *AIDS Res Hum Retroviruses* 13:1007-15). Interestingly, this analysis suggested two substitutions, Gln20Ala and Thr25Ala.

Once these mutations were introduced into the miniprotein (CD4M8, FIG. 2), it increased its binding affinity for gp120 by more than one order of magnitude (Vita (1999) *Proc Natl Acad Sci USA* 96(23):13091-6). Three more mutations, Leu18Lys, Ser9Arg, Pro28 were suggested by the structural analysis and when these mutations were incorporated, the binding affinity was increased further by ten-fold as compared to previous double mutant (CD4M8). These 5 mutations produced an optimized mini-CD4 (CD4M9, FIG. 2) that improved binding to gp120 with an IC50 of 400 nM. CDM33 is a 27 amino acid mimic of CD4 and is described in Martin et al. (2003) *Nature Biotech.* 21:71-76.

Example 3

Additional Rationally Designed Mini CD4 Proteins

As described in Vita et al. (1999) *Proc Natl Acad Sci USA* 96(23):13091-6 and Martin et al. (2003) *Nat. Biotech.* 21:71-76, further rationally designed mini CD4 proteins are made by introducing an azido photo-reactive function on the distal (para) position of the Phe23 phenyl ring, which, by analogy with sCD4 Phe43, should block the entrance of the gp120 hydrophobic "Phe43 cavity." The azido photo-reactive function can be easily produced chemically from the commercially available p-amino-phenylalanine and, upon irradiation at 250 nm, forms a reactive nitrene moiety that undergoes fast insertion reaction in electron-rich amino acid side chains (e.g., aromatic side chains), which are indeed numerous in the hydrophobic "Phe43 cavity." Alternatively, a haloacetamide group, reactive to methionine or histidine residues, present close to the "Phe43 cavity," is incorporated on the p-amino-phenylalanine 23 or on another position at the interface. Because of the strategic position of the Phe23 side chain, penetrating the deep "Phe43 cavity" of gp120, the photo- or chemical reaction results in a relatively homogeneous and high yields covalent complex.

Example 4

Engineering and Biological Expression of CD4 Miniprotein-Envelope Fusion Proteins Polynucleotides encoding the following CD4 mini protein sequences are cloned into an expression construct comprising a sequence encoding an HIV Env polypeptide (e.g., a sequence encoding a modified gp120-encoding polynucleotide as described, for instance in International Publications WO 00/39302 and WO 03/020876):

(SEQ ID NO: 1)
gggggTCTASQQKKSIQFHWKNSNQIKILGNQGSFLTKGPSKLNIRADSR
RSLWDQGNFPLIIKNLKIEDSDTYICEVEDQKEEVQLggggg (SEQ ID NO: 2)
gggggQKKSIQFHWKNSNQIKILGNQGSFLTKGPSKLNIRADSRRSLWDQ
GNFPLIIKNLKIEDSDTYICEggggg (SEQ ID NO: 3)
gggggNSNQIKILGNQGSFLTKGPSKLNIRADSRRSLWDQGNggggg (SEQ ID NO: 4)
gggggGNQGSFLTKGPSKLNIRADSRRSLWDQGNggggg In these sequences, residues marked by underlining are the actual residues that are in contact with gp120 and residues shown in lower case ("g" for glycine) are linker residues that provide flexibility to gp120-CD4 for making a complex.

Any of SEQ ID NO:1-4 are inserted in place of V1, V2, V3, V4 and/or V5 loops of a Env-encoding sequences, for example the gp120-encoding sequence shown in FIG. 7 (SEQ ID NO:5). Thus, the insertion can be made into any one of the V-loops and, in addition, the construct may have one or more additional loops deleted. V1 and V2, in particular are relatively close to the CD4 binding site and can be deleted in the core protein in the oligomeric $gp140_{SF162}$, without loss of stability and binding function. Kwong et al., supra. Shorter insertions (e.g., corresponding to the CDR2-like loop only) may also be also inserted in place of one or more variable regions. Models of the Env-CD4 hybrids are produced by using the CD4M9-$gp120_{HXB2}$ model structure used to optimize CD4 miniprotein binding affinity (see above) and deduced from the CD4-$gp120_{HXB2}$ structure. Different linker sequences are tested (e.g., to minimize energy). The hybrids (chimeras) with the lowest energies will be further analyzed and compared with the non-covalent complex structures. Chimeras with the simple insertion of CD4 CDR2-like region will be treated similarly.

In addition, a 27 amino acid CD4 mini protein as described in Martin et al. (2003) *Nat Biotechnol* January:21(1):71-6 is inserted into the V1 or V2 loops. The stability and folding efficiency of the mimetic scaffold suggest that, if sufficient flexibility is allowed at the V-loop insertion sites, the CD4 miniprotein will fold properly, once inserted into the protein envelope.

Expression is followed by standard techniques. Further, the binding of CD4 protein to Env is monitored by the induction of CD4 inducible epitopes recognized by MAbs 17b and 4.8d using standard techniques. In particular, purified chimeras produced in the SF162 Env background, then, are characterized by SPR to evaluate exposure of CD41 epitopes and by co-receptor binding tests to evaluate their binding affinities. In competitive ELISA, a rationally designed miniprotein was able to specifically bind gp120 at an IC50 of 40 uM, which are four orders of magnitude higher than that of sCD4. See, also Devico et al. (19969) *Virology* 218:258-263 and Zhang et al. (1999) *Biochemistry* 38(29):9405-16 which show surface plasmon resonance (SPR) testing of another CD4 miniprotein and that the CD4 miniproteins are able to compete with sCD4 for binding to the same gp120 site, and to induce envelope conformational changes, as detected by the monoclonal antibody 17b (Sullivan et al. (1998) *J Virol* 72(8):6332-6338). This antibody recognizes an epitope located near the gp120 V3 loop and consisting mainly of the conserved stem of V1/V2, which is probably masked by the flanking V1/V2 and V3 loops (Kwong et al. (1998) *Nature* (London) 393:648-659; Rizzuto et al. (1998) *Science* 280:1949-1953) but exposed in the gp120 complexed to CD4. The effect of miniprotein addition on antibody maximum binding and association rate increase was small, probably reflecting its low gp120 binding affinity, but specific and easily detected.

In sum, these results demonstrate that i) a significant portion of gp120 binding surface of CD4 can be reproduced in a miniprotein system, and ii) the engineered CD4 mimic and/or CD4-Env hybrids contain enough CD4 structural elements able to induce gp120 conformational changes, similar to those expressed by sCD4.

Electroporation and other methods described herein are used to efficiently deliver polynucleotides encoding the fusion proteins to non-human primates. The DNA prime/protein boost strategy allows for screening of multiple Env structures in rabbits and non-human primates with the potential for epitope presentation in situ in the host when delivered as DNA vaccines.

Example 5

Neutralizing Antibody Production Using CD4-Env Complexes

A. Env-sCD4 Complexes

Figure 5:
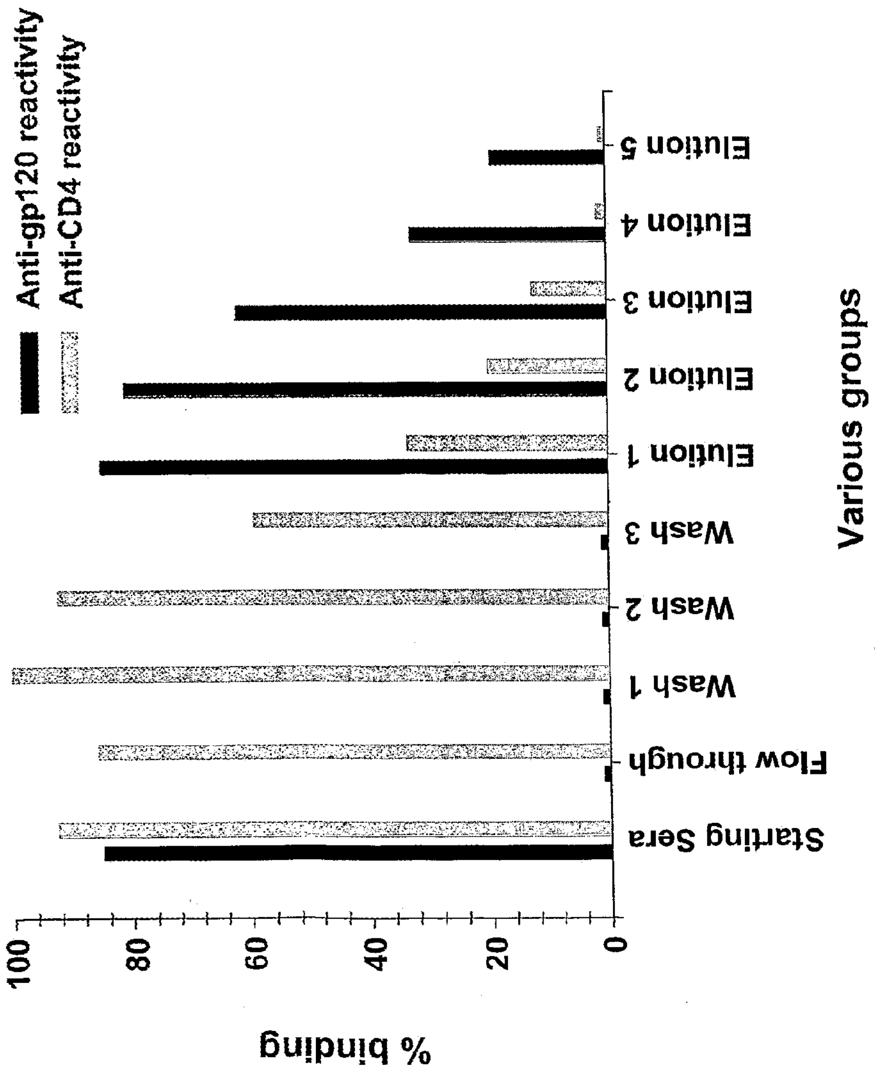
FIG. 5 is a bar graph depicting reactivities against gp120 and of CD4 affinity purified antibodies. The left bar of each set shows anti-gp120 reactivity and the right bar of each set shows anti-CD4 reactivity.
Figure 6:
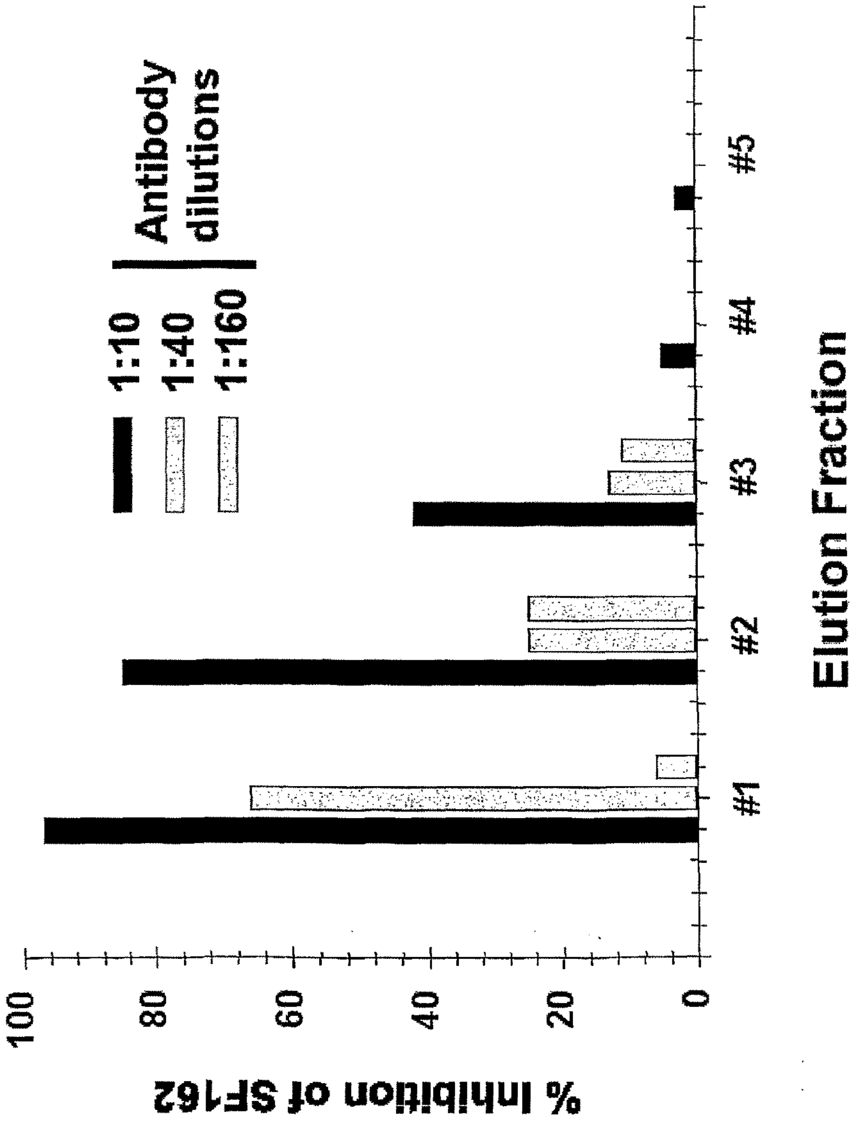
FIG. 6 is bar graph depicting primary isolate neutralizing antibody activity of gp120 column fractions. The left bar of each set shows activity at 1:10 dilution; the center bar shows activity at 1:40 dilution and the right bar shows activity at 1:160 dilution.

Rabbit sera were tested in neutralizing assays both against the T-cell adapted (TCLA) as well as primary HIV-1 strains. Antibodies induced in these rabbits by the gp120-sCD4 complexes were able to neutralize both the SF162 primary isolate as well as T-cell adapted isolates, SF2 (homologous strain) and RF (heterologous). To demonstrate that anti-gp120 antibodies were responsible for neutralizing the virus, an SF2 gp120 affinity column was used to purify the Env-specific antibody fractions from these sera. The majority of anti-gp120 specific antibodies (95%) bound to the gp120 affinity columns. These were eluted with 200 mom Glycine pH 2.5. Anti-CD4 antibodies did not efficiently bind to the affinity column. Affinity purified anti-gp120 antibodies were further evaluated for their anti-gp120 and anti-CD4 reactivities in ELISA as well as in an HPLC based assay. Using this strategy, approximately 90% of the anti-gp120 antibodies were affinity purified, however column eluted gp120 specific antibody fractions were slightly contaminated with antibodies specific to CD4 (FIG. 5). Accordingly, affinity purified anti-gp120 specific antibodies were further purified by passage over a CD4 affinity column to absorb anti-CD4 antibodies. After absorption, anti-gp120 affinity purified antibodies were free from any detectable anti-CD4 antibodies. These affinity purified anti-gp120 antibodies were able to neutralize both subtype B and C primary HIV-1 isolates (FIG. 6 and Table 1, below). The values shown in Table 1 represent the reciprocal of the highest dilution at which 50% virus inhibition was observed in a PBMC-based virus neutralization assay (by Dr. Carl Wild at Panics Corporation, Gaithersburg, Md.).

TABLE 1

Neutralizing activity of gp120 column fractions against HIV-1 subtype B and C primary isolates

| Elution Fraction | HIV-$1_{12298P}$ (Subtype B) | HIV-$1_{3899S}$ (Subtype C) |
|---|---|---|
| 1 | 25 | 62 |
| 2 | 26 | 39 |
| 3 | 32 | <20 |

B. Rationally-Designed Mini CD4 Protein-Env Complexes

Two rabbits each were immunized with fixed or unfixed gp120-sCD4 complexes (prepared as described in Example 1) in MF59 at 0, 4, 12 and 24 weeks. Sera were collected biweekly and analyzed against SF2 gp120 in an ELISA. These animals mounted a strong immune response against gp120 (FIG. 3A). In general, fixed (e.g., formalin-fixed) complexes were more immunogenic as reflected by high antibody titers obtained in this group compared to the group that received unfixed complexes. In addition to anti-gp120 responses, these complexes also induced strong anti-CD4 response, as expected (FIG. 3B)

Thus, the rationally designed CD4 miniprotein, bound with high affinity to different envelope forms (including oligomeric and monomeric forms of SF162 with and without V2-deletes), induced conformational changes in these proteins as efficiently as sCD4, and induced full exposition of conserved cryptic CD4 inducible epitopes and/or co-receptor binding sites. Thus, the optimized CD4 miniprotein appears to represent a fully functional substitute of sCD4 and that engineering further CD4 miniproteins may result in surrogate molecules that may be useful in complex with envelope protein to expose envelope epitopes to neutralizing antibodies thus may find potential application in vaccine formulations.

C. Env-CD4 Hybrids Proteins

Two rabbits each are immunized with constructs encoding Env-CD4 hybrids at 0, 4, 12 and 24 weeks. Sera are collected biweekly and analyzed in an ELISA. Env-CD4 hybrid proteins (and polynucleotides encoding these hybrids) are expected to represent a fully functional substitute of sCD4 and may be useful in expose envelope epitopes to neutralizing antibodies thus may find potential application in vaccine formulations.

D. Monkeys

Groups of 5 rabbits are immunized with Env-CD4 miniprotein complexes or Env-CD4 hybrid proteins with adjuvant (MF59) along with control groups of Env protein only and CD4 miniprotein only. CD4 complexes and Env-CD4 hybrids are made with monomeric and oligomeric forms of SF162 Env with and without V2-deletes and the antibody responses in rabbits compared. Immunization schedules are at 0, 4, and 24 week immunizations; when warranted, an additional booster may be included at 24 weeks. Env-CD4 complexes identified by these rabbit studies are then tested in macaques.

Example 6

Unmasking Cryptic Epitopes of gp41 Subunit in Oligomeric Envelopes

CD4 miniprotein induces a conformational transformation of oligomeric (o-gp140) envelopes, unmasking cryptic epitopes, close to co-receptor sites in gp120 subunit and efficiently increases co-receptor binding affinity in different gp120 envelopes. Whether this conformational transformation can also expose epitopes within the gp41 subunit of o-gp140 envelopes has not been tested. Accordingly, the induction of this conformational transformation by CD4 miniproteins binding in the different oligomeric Env structures is tested, using SPR technology and 2F5 mAb or DP178 peptides (or congeners). The effect of addition of peptides from the N-terminal domain of CCR5 co-receptor, which have been shown to bind to gp120 is also examined.

If exposition of gp41 epitopes is demonstrated, the peptides are chemically coupled to the CD4 miniprotein, to produce novel bi-functional ligands, presenting increased potency in unmasking gp41 epitopes. Novel chimeric oligomeric envelopes, incorporating the bi-functional ligands are also produced chemically or genetically, and tested. Candidate envelope proteins with superior exposure of gp120 and gp41 cryptic epitopes are then tested in animals for the induction of neutralizing antibodies.

Example 7

Production of Monoclonal Antibodies Targeting Cryptic Conserved Epitopes of Env Selected Env-CD4 immunogens will be injected in rats to prepare monoclonal antibodies, according to the standard procedures. Clones will be screened in ELISA against CD4 miniprotein-gp120 complex, CD4 miniprotein-o-gp140, gp120 and o-gp140 alone and CD4M33 miniprotein as well. All the clones exhibiting highest affinity for complexes as compared to envelopes alone will be further tested in Biacore. All the clones scoring positive in Biacore against the CD4M33-gp120 and or CD4M33-o-gp140 complexes will be selected and used for bulk production of ascites fluids.

The invention claimed is:

1. A method of inducing an immune response in a subject, comprising:

administering a first composition comprising a polynucleotide encoding a hybrid human immunodeficiency virus (HIV) envelope (Env)-CD4 protein; and administering a second composition comprising the hybrid human HIV Env-CD4 protein in an amount sufficient to induce an immune response in the subject, wherein the hybrid HIV Env-CD4 protein comprises: (1) an HIV Env polypeptide which comprises a CD4-binding site and a deletion region from which one or more variable (V) regions are deleted; and (2) a CD4 mini-protein or a CD4-mimetic inserted into the deletion region, wherein the CD4 mini-protein or CD4-mimetic maintains the structural conformation of a CDR2-like loop; and wherein the insertion of the CD4 mini-protein or the CD4 mimetic leads to exposure of a cryptic HIV envelope epitope in or near the CD4-binding site or in or near the chemokine receptor-binding site.

2. The method of claim 1, wherein the hybrid Env-CD4 protein comprises the CD4 mini-protein.

3. The method of claim 1, wherein the hybrid Env-CD4 protein comprises the CD4 mimetic.

4. The method of claim 1, wherein the deletion region comprises a deletion in V1.

5. The method of claim 1, wherein the deletion region comprises a deletion in V2.

6. The method of claim 1, further comprising one or more linker sequences.

7. The method of claim 6, wherein the one or more linker sequences flank the CD4 mini-protein or the CD4 mimetic.

8. The method of claim 1, wherein the CD4 mini-protein comprises the amino acid sequence SEQ ID NO:1.

9. The method of claim 1, wherein the CD4 mini-protein comprises the amino acid sequence SEQ ID NO:2.

10. The method of claim 1, wherein the CD4 mini-protein comprises the amino acid sequence SEQ ID NO:3.

11. The method of claim 1, wherein the CD4 mini-protein comprises the amino acid sequence SEQ ID NO:4.

12. The method of claim 1, wherein the HIV Env polypeptide comprises gp140.

13. The method of claim 1, wherein the first composition comprises a vector encoding the polynucleotide.

14. The method of claim 13, wherein the vector is a non-viral vector.

15. The method of claim 13, wherein the vector is a recombinant viral vector.

16. The method of claim 15, wherein the viral vector is a retroviral vector.

17. The method of claim 15, wherein the viral vector is an alphaviral vector.

18. The method of claim 15, wherein the viral vector is an adenoviral vector.

19. The method of claim 15, wherein the viral vector is an adeno-associated viral vector.

20. The method of claim 15, wherein the viral vector is a pox viral vector.

21. The method of claim 15, wherein the viral vector is an avipox viral vector.

22. The method of claim 1, wherein the polynucleotide is delivered using a particulate carrier.

23. The method of claim 22, wherein the polynucleotide is coated on a gold or tungsten particle and the coated particle is delivered to the subject using a gene gun.

24. The method of claim 1, wherein the polynucleotide is encapsulated in a liposome preparation.

25. The method of claim 1, wherein the subject is a mammal.

26. The method of claim 1, wherein the mammal is a human.

27. The method of claim 1, wherein the first composition further comprises an adjuvant.

28. The method of claim 1, wherein the second composition further comprises an adjuvant.

* * * * *